United States Patent
Richards et al.

(10) Patent No.: US 6,194,211 B1
(45) Date of Patent: *Feb. 27, 2001

(54) TRANSCRIPTIONAL REGULATORY SEQUENCE OF CARCINOEMBRYONIC ANTIGEN FOR EXPRESSION TARGETING

(75) Inventors: Cynthia Ann Richards; Brian Huber, both of Durham, NC (US)

(73) Assignee: Glaxo Wellcome Inc., Research Triangle Park, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 11 days.

This patent is subject to a terminal disclaimer.

(21) Appl. No.: 08/646,301

(22) PCT Filed: Nov. 18, 1994

(86) PCT No.: PCT/GB94/02546

§ 371 Date: May 16, 1996

§ 102(e) Date: May 16, 1996

(87) PCT Pub. No.: WO95/14100

PCT Pub. Date: May 26, 1995

(51) Int. Cl.$^7$ ........................ C12N 15/63; C12N 15/867; C12N 5/10; C07H 21/04
(52) U.S. Cl. ........................ 435/456; 435/455; 435/320.1; 435/325; 536/23.1; 536/23.2; 536/23.4; 536/23.5; 536/23.7; 424/93.1; 424/93.2; 424/93.6
(58) Field of Search .......................... 435/69.1, 172.1, 435/172.3, 325, 327, 366, 320.1, 455, 456; 514/44; 424/93.2, 93.6, 93.1; 536/23.1, 23.2, 23.4, 23.5, 23.7, 24.1

(56) References Cited

U.S. PATENT DOCUMENTS 5,691,177 * 11/1997 Guber et al. ....................... 435/172.3

OTHER PUBLICATIONS

Anderson, Nature, vol. 392, pp. 25–30, Apr. 30, 1998.*
Verma et al., Nature, vol. 389, pp. 239–242, Sep. 18, 1997.*
Fox, Nature Biotechnology, vol. 18, pp. 143–144, Feb. 18, 2000.*
Ross et al., Human Gene Therapy, vol. 7, pp. 1781–1790, Sep. 10, 1996.*
Thompson et al., PNAS, vol. 84, pp. 2965–2969, May 1987.*
Borrelli et al., PNAS, vol. 85, Oct. 1988, pp. 7572–7576.*
Moolton, Medical Hypotheses, vol. 24, 1987, pp. 43–51.*
Andersen et al., Arch. Microbiol., vol. 152, 1989, pp. 115–118.*
Nishiyama et al., Cancer Res., vol. 45, Apr. 1985, pp. 1753–1761.*
Miller et al., BioTechniques, vol. 7, No. 9, 1989, pp. 980–990.*
Willcocks et al., Characterization of the genomic organization of human carcinoembryonic antigen (CEA). *Genomics* 8:492–500 (1990).
Zimmermann et al., Isolation and characterization of cDNA clones encoding the human carcinoembryonic antigen reveal a highly conserved repeating structure. *Proc. Natl. Acad. Sci.* 84:2960–2964 (1987).
Rudert et al., Characterization of murine carcinoembryonic antigen gene family members. *Mammalian Genome* 3:262–273 (1992).
Rudert et al. Ubiquitous nuclear factors bind specifically to a 5'-region conserved in carcinoembryonic antigen–related genes. *Biochemical and Biophysical Research Communications* 185:893–901 (1992).
Richards, C. A. et al., "The Transcriptional Control Region of the Human Carcinoembryonic antigen gene: DNA Sequence and Homology Studies", DNA Sequence, 4(3), 185–196 [Jul. 1993], Switzerland.
Schrewe, H. et al., "Cloning of the Complete Gene for Carcinoembryonic Antigen: Analysis of Its Promoter Indicates a Region Conveying Cell–Type Specific Expression", Molecular and Cellular Biology, 10(6), 2738–2748 [Jun. 1990].
Huber, B. E. et al., "Virus–Directed Enzyme/Prodrug Therapy (VDEPT): Selectively Engineering Drug Sensitivity Into Tumors", Annals of the New York Academy of Sciences, 716, 104–114, [1994] (see the whole document and Gene Therapy For Neoplastic Disease Jun. 26–29, 1993, Washington, USA).
Sikora, K., "Gene Therapy for Cancer", Trends in Biotechnology, 11(5), 197–201 [May 1993], Cambridge, GB.
Harris, J. D. et al., "Gene Therapy for Cancer Using Tumour–Specific Prodrug Activation", Gene Therapy, 1(3), 170–175 [May 1994].
Huber, B. E. et al., "Gene Therapy for Cancer Using Tumour–Specific Prodrug Activation", Gene Therapy, 1(3), 170–175 [May, 1994].
Tadashi, Osaki et al., "Gene Therapy For Carcinoembryonic Antigen–Producing Human Lung Cancer Cells By Cell Type–Specific Expression of Herpes Simplex Virus Thymidine Kinase Gene", Cancer Research, 54(20), 5258–5261 [Oct. 15, 1994].

* cited by examiner

Primary Examiner—David Guzo
(74) Attorney, Agent, or Firm—Virginia C. Bennett

(57) ABSTRACT

The transcriptional regulatory sequence (TRS) of Carcinoembryonic Antigen (CEA) and molecular chimeras comprising the CEA TRS and DNA encoding a heterologous enzyme are described. Such molecular chimeras are capable of targeting the expression of the heterologous enzyme to CEA-positive cells. The heterologous enzyme may be cytosine deaminase.

25 Claims, 20 Drawing Sheets cos CEA1 MAP AND SEQUENCE FROM SCHREWE, et.al. Mol Cell Biol 10:2738,1990

| Plasmid | CEA Coordinates |
|---|---|
| pCR113 | (−299 to +69) |
| pCR105 | (−1664 to +69) |
| pCR145 | (−14462 to −10691)+(−299 to +69) |
| pCR148 | (−89 to −40)+(−90 to +69) |
| pCR158 | [3 X (−89 to −40)]+(−90 to +69) |
| pCR136 | (−3919 to −6071) + (−299 to +69) |
| pCR137 | (−6071 to −3919) + (−299 to +69) |
| pCR162 | (−13579 to −10691)+(−89 to −40)+(−90 to +69) |
| pCR163 | (−10691 to −13579)+(−89 to −40)+(−90 to +69) |

*Fig. 5B*

```
-14463  AAGCTTTTTA GTGCTTTAGA CAGTGAGCTG GTCTGTCTAA CCCAAGTGAC CTGGGCTC
-14403  TACTCAGCCC CAGAAGTGAA GGGTGAAGCT GGGTGGAGCC AAACCAGGCA AGCCTACC
-14343  CAGGGCTCCC AGTGGCCTGA GAACCATTGG ACCCAGGACC CATTACTTCT AGGGTAAG
-14283  AGGTACAAAC ACCAGATCCA ACCATGGTCT GGGGGACAG CTGTCAAATG CCTAAAAA
-14223  TACCTGGGAG AGGAGCAGGC AAACTATCAC TGCCCCAGGT TCTCTGAACA GAAACAGA
-14163  GGCAACCCAA AGTCCAAATC CAGGTGAGCA GGTGCACCAA ATGCCCAGAG ATATGACG
-14103  GCAAGAAGTG AAGGAACCAC CCCTGCATCA AATGTTTTGC ATGGGAAGGA GAAGGGGG
-14043  GCTCATGTTC CCAATCCAGG AGAATGCATT TGGGATCTGC CTTCTTCTCA CTCCTTGG
-13983  AGCAAGACTA AGCAACCAGG ACTCTGGATT TGGGGAAAGA CGTTTATTTG TGGAGGCC
-13923  TGATGACAAT CCCACGAGGG CCTAGGTGAA GAGGGCAGGA AGGCTCGAGA CACTGGGG
-13863  TGAGTGAAAA CCACACCCAT GATCTGCACC ACCCATGGAT GCTCCTTCAT TGCTCACC
-13803  TCTGTTGATA TCAGATGGCC CCATTTTCTG TACCTTCACA GAAGGACACA GGCTAGGG
-13743  TGTGCATGGC CTTCATCCCC GGGGCCATGT GAGGACAGCA GGTGGGAAAG ATCATGGG
-13683  CTCCTGGGTC CTGCAGGGCC AGAACATTCA TCACCCATAC TGACCTCCTA GATGGGAA
-13623  GCTTCCCTGG GGCTGGGCCA ACGGGGCCTG GCAGGGGAG AAAGGACGTC AGGGGACA
-13563  GAGGAAGGGT CATCGAGACC CAGCCTGGAA GGTTCTTGTC TCTGACCATC CAGGATTT
-13503  TTCCCTGCAT CTACCTTTGG TCATTTTCCC TCAGCAATGA CCAGCTCTGC TTCCTGAT
-13443  CAGCCTCCCA CCCTGGACAC AGCACCCCAG TCCCTGGCCC GGCTGCATCC ACCCAATA
-13383  CTGATAACCC AGGACCCATT ACTTCTAGGG TAAGGAGGGT CCAGGAGACA GAAGCTGA
-13323  AAAGGTCTGA AGAAGTCACA TCTGTCCTGG CCAGAGGGGA AAAACCATCA GATGCTGA
-13263  CAGGAGAATG TTGACCCAGG AAAGGGACCG AGGACCCAAG AAAGGAGTCA GACCACCA
-13203  GTTTGCCTGA GAGGAAGGAT CAAGGCCCCG AGGGAAAGCA GGGCTGGCTG CATGTGCA
```

*Fig.6 (1/11)*

```
-13143  ACACTGGTGG GGCATATGTG TCTTAGATTC TCCCTGAATT CAGTGTCCCT GCCATGGC
-13083  GACTCTCTAC TCAGGCCTGG ACATGCTGAA ATAGGACAAT GGCCTTGTCC TCTCTCCC
-13023  CCATTTGGCA AGAGACATAA AGGACATTCC AGGACATGCC TTCCTGGGAG GTCCAGGT
-12963  TCTGTCTCAC ACCTCAGGGA CTGTAGTTAC TGCATCAGCC ATGGTAGGTG CTGATCTC
-12903  CCAGCCTGTC CAGGCCCTTC CACTCTCCAC TTTGTGACCA TGTCCAGGAC CACCCCTC
-12843  ATCCTGAGCC TGCAAATACC CCCTTGCTGG GTGGGTGGAT TCAGTAAACA GTGAGCTC
-12783  ATCCAGCCCC CAGAGCCACC TCTGTCACCT TCCTGCTGGG CATCATCCCA CCTTCACA
-12723  CACTAAAGAG CATGGGGAGA CCTGGCTAGC TGGGTTTCTG CATCACAAAG AAAATAAT
-12663  CCCAGGTTCG GATTCCCAGG GCTCTGTATG TGGAGCTGAC AGACCTGAGG CCAGGAGA
-12603  GCAGAGGTCA GCCCTAGGGA GGGTGGGTCA TCCACCCAGG GGACAGGGGT GCACCAGC
-12543  TGCTACTGAA AGGGCCTCCC CAGGACAGCG CCATCAGCCC TGCCTGAGAG CTTTGCTA
-12483  CAGCAGTCAG AGGAGGCCAT GGCAGTGGCT GAGCTCCTGC TCCAGGCCCC AACAGACC
-12423  ACCAACAGCA CAATGCAGTC CTTCCCCAAC GTCACAGGTC ACCAAAGGGA AACTGAGG
-12363  CTACCTAACC TTAGAGCCAT CAGGGGAGAT AACAGCCCAA TTTCCAAAC AGGCCAGT
-12303  CAATCCCATG ACAATGACCT CTCTGCTCTC ATTCTTCCCA AAATAGGACG CTGATTCT
-12243  CCCACCATGG ATTTCTCCCT TGTCCCGGGA GCCTTTTCTG CCCCCTATGA TCTGGGCA
-12183  CCTGACACAC ACCTCCTCTC TGGTGACATA TCAGGGTCCC TCACTGTCAA GCAGTCCA
-12123  AAGGACAGAA CCTTGGACAG CGCCCATCTC AGCTTCACCC TTCCTCCTTC ACAGGGTT
-12063  GGGCAAAGAA TAAATGGCAG AGGCCAGTGA GCCCAGAGAT GGTGACAGGC AGTGACCC
-12003  GGGCAGATGC CTGGAGCAGG AGCTGGCGGG GCCACAGGGA GAAGGTGATG CAGGAAGG
-11943  AACCCAGAAA TGGGCAGGAA AGGAGGACAC AGGCTCTGTG GGGCTGCAGC CCAGGGTT
-11883  ACTATGAGTG TGAAGCCATC TCAGCAAGTA AGGCCAGGTC CCATGAACAA GAGTGGGA
-11823  ACGTGGCTTC CTGCTCTGTA TATGGGGTGG GGGATTCCAT GCCCCATAGA ACCAGATG
```

Fig. 6 (2/11)

```
-11763  CGGGGTTCAG ATGGAGAAGG AGCAGGACAG GGGATCCCCA GGATAGGAGG ACCCCAGT

-11703  CCCCACCCAG GCAGGTGACT GATGAATGGG CATGCAGGGT CCTCCTGGGC TGGGCTCT

-11643  CTTTGTCCCT CAGGATTCCT TGAAGGAACA TCCGGAAGCC GACCACATCT ACCTGGTG

-11583  TTCTGGGGAG TCCATGTAAA GCCAGGAGCT TGTGTTGCTA GGAGGGGTCA TGGCATGT

-11523  TGGGGGCACC AAAGAGAGAA ACCTGAGGGC AGGCAGGACC TGGTCTGAGG AGGCATGG

-11463  GCCCAGATGG GGAGATGGAT GTCAGGAAAG GCTGCCCCAT CAGGGAGGGT GATAGCAA

-11403  GGGGGTCTGT GGGAGTGGGC ACGTGGGATT CCCTGGGCTC TGCCAAGTTC CCTCCCAT

-11343  TCACAACCTG GGACACTGC CCATGAAGGG GCGCCTTTGC CAGCCAGAT GCTGCTGG

-11283  CTGCCCATCC ACTACCCTCT CTGCTCCAGC CACTCTGGGT CTTTCTCCAG ATGCCCTG

-11223  CAGCCCTGGC CTGGGCCTGT CCCTGAGAG GTGTTGGGAG AAGCTGAGTC TCTGGGGA

-11163  CTCTCATCAG AGTCTGAAAG GCACATCAGG AAACATCCCT GGTCTCCAGG ACTAGGCA

-11103  GAGGAAAGGG CCCCAGCTCC TCCCTTTGCC ACTGAGAGGG TCGACCCTGG GTGGCCAC

-11043  TGACTTCTGC GTCTGTCCCA GTCACCCTGA AACCACAACA AAACCCCAGC CCCAGACC

-10983  GCAGGTACAA TACATGTGGG GACAGTCTGT ACCCAGGGGA AGCCAGTTCT CTCTTCCT

-10923  GAGACCGGGC CTCAGGGCTG TGCCCGGGGC AGGCGGGGGC AGCACGTGCC TGTCCTTG

-10863  AACTCGGGAC CTTAAGGGTC TCTGCTCTGT GAGGCACAGC AAGGATCCTT CTGTCCAG

-10803  ATGAAAGCAG CTCCTGCCCC TCCTCTGACC TCTTCCTCCT TCCCAAATCT CAACCAAC

-10743  ATAGGTGTTT CAAATCTCAT CATCAAATCT TCATCCATCC ACATGAGAAA GCTTAAAA

-10683  CAATGGATTG ACAACATCAA GAGTTGGAAC AAGTGGACAT GGAGATGTTA CTTGTGGA

-10623  TTTAGATGTG TTCAGCTATC GGGCAGGAGA ATCTGTGTCA AATTCCAGCA TGGTTCAG

-10563  GAATCAAAAA GTGTCACAGT CCAAATGTGC AACAGTGCAG GGGATAAAAC TGTGGTGC

-10503  TCAAACTGAG GGATATTTTG GAACATGAGA AAGGAAGGGA TTGCTGCTGC ACAGAACA

-10443  GATGATCTCA CACATAGAGT TGAAAGAAAG GAGTCAATCG CAGAATAGAA AATGATCA
```

*Fig.6 (3/11)*

```
-10383  AATTCCACCT CTATAAAGTT TCCAAGAGGA AAACCCAATT CTGCTGCTAG AGATCAGA
-10323  GGAGGTGACC TGTGCCTTGC AATGGCTGTG AGGGTCACGG GAGTGTCACT TAGTGCAG
-10263  AATGTGCCGT ATCTTAATCT GGGCAGGGCT TTCATGAGCA CATAGGAATG CAGACATT
-10203  TGCTGTGTTC ATTTTACTTC ACCGGAAAAG AAGAATAAAA TCAGCCGGGC GCGGTGGC
-10143  ACGCCTGTAA TCCCAGCACT TTAGAAGGCT GAGGTGGGCA GATTACTTGA GGTCAGGA
-10083  TCAAGACCAC CCTGGCCAAT ATGGTGAAAC CCCGGCTCTA CTAAAAATAC AAAAATTA
-10023  TGGGCATGGT GGTGCGCGCC TGTAATCCCA GCTACTCGGG AGGCTGAGGC TGGACAAT
 -9963  CTTGGACCCA GGAAGCAGAG GTTGCAGTGA GCCAAGATTG TGCCACTGCA CTCCAGCT
 -9903  GGCAACAGAG CCAGACTCTG TAAAAAAAAA AAAAAAAAAA AAAAAAGAA AGAAAGAA
 -9843  AGAAAAGAAA GTATAAAATC TCTTTGGGTT AACAAAAAAA GATCCACAAA ACAAACAC
 -9783  GCTCTTATCA AACTTACACA ACTCTGCCAG AGAACAGGAA ACACAAATAC TCATTAAC
 -9723  ACTTTTGTGG CAATAAAACC TTCATGTCAA AAGGAGACCA GGACACAATG AGGAAGTA
 -9663  ACTGCAGGCC CTACTTGGGT GCAGAGAGGG AAAATCCACA ATAAAACAT TACCAGAA
 -9603  AGCTAAGATT TACTGCATTG AGTTCATTCC CCAGGTATGC AAGGTGATTT TAACACCT
 -9543  AAATCAATCA TTGCCTTTAC TACATAGACA GATTAGCTAG AAAAAAATTA CAACTAGC
 -9483  AACAGAAGCA ATTTGGCCTT CCTAAAATTC CACATCATAT CATCATGATG GAGACAGT
 -9423  AGACGCCAAT GACAATAAAA AGAGGGACCT CCGTCACCCG GTAAACATGT CCACACAG
 -9363  CCAGCAAGCA CCCGTCTTCC CAGTGAATCA CTGTAACCTC CCCTTTAATC AGCCCCAG
 -9303  AAGGCTGCCT GCGATGGCCA CACAGGCTCC AACCCGTGGG CCTCAACCTC CCGCAGAG
 -9243  TCTCCTTTGG CCACCCCATG GGGAGAGCAT GAGGACAGGG CAGAGCCCTC TGATGCCC
 -9183  ACATGGCAGG AGCTGACGCC AGAGCCATGG GGGCTGGAGA GCAGAGCTGC TGGGGTCA
 -9123  GCTTCCTGAG GACACCCAGG CCTAAGGGAA GGCAGCTCCC TGGATGGGGG CAACCAGG
 -9063  CCGGGCTCCA ACCTCAGAGC CCGCATGGGA GGAGCCAGCA CTCTAGGCCT TTCCTAGG
```

Fig.6 (4/11)

```
-9003  GACTCTGAGG GGACCCTGAC ACGACAGGAT CGCTGAATGC ACCCGAGATG AAGGGGCC

-8943  CACGGGACCC TGCTCTCGTG GCAGATCAGG AGAGAGTGGG ACACCATGCC AGGCCCCC

-8883  GGCATGGCTG CGACTGACCC AGGCCACTCC CCTGCATGCA TCAGCCTCGG TAAGTCAC

-8823  GACCAAGCCC AGGACCAATG TGGAAGGAAG GAAACAGCAT CCCCTTTAGT GATGGAAC

-8763  AAGGTCAGTG CAAAGAGAGG CCATGAGCAG TTAGGAAGGG TGGTCCAACC TACAGCAC

-8703  ACCATCATCT ATCATAAGTA GAAGCCCTGC TCCATGACCC CTGCATTTAA ATAAACGT

-8643  GTTAAATGAG TCAAATTCCC TCACCATGAG AGCTCACCTG TGTGTAGGCC CATCACAC

-8583  ACAAACACAC ACACACACAC ACACACACAC ACACACACAC ACAGGGAAAG TGCAGGAT

-8523  TGGACAGCAC CAGGCAGGCT TCACAGGCAG AGCAAACAGC GTGAATGACC CATGCAGT

-8463  CCTGGGCCCC ATCAGCTCAG AGACCCTGTG AGGGCTGAGA TGGGGCTAGG CAGGGGAG

-8403  ACTTAGAGAG GGTGGGGCCT CCAGGGAGGG GGCTGCAGGG AGCTGGGTAC TGCCCTCC

-8343  GGAGGGGGCT GCAGGGAGCT GGGTACTGCC CTCCAGGGAG GGGGCTGCAG GGAGCTGG

-8283  ACTGCCCTCC AGGGAGGGGG CTGCAGGGAG CTGGGTACTG CCCTCCAGGG AGGGGGCT

-8223  AGGGAGCTGG GTACTGCCCT CCAGGGAGGC AGGAGCACTG TTCCCAACAG AGAGCACA

-8163  TTCCTGCAGC AGCTGCACAG ACACAGGAGC CCCCATGACT GCCCTGGGCC AGGGTGTG

-8103  TTCCAAATTT CGTGCCCCAT TGGGTGGGAC GGAGGTTGAC CGTGACATCC AAGGGGCA

-8043  TGTGATTCCA AACTTAAACT ACTGTGCCTA CAAAATAGGA AATAACCCTA CTTTTTCT

-7983  TATCTCAAAT TCCCTAAGCA CAAGCTAGCA CCCTTTAAAT CAGGAAGTTC AGTCACTC

-7923  GGGGTCCTCC CATGCCCCCA GTCTGACTTG CAGGTGCACA GGGTGGCTGA CATCTGTC

-7863  TGCTCCTCCT CTTGGCTCAA CTGCCGCCCC TCCTGGGGGT GACTGATGGT CAGGACAA

-7803  GATCCTAGAG CTGGCCCCAT GATTGACAGG AAGGCAGGAC TTGGCCTCCA TTCTGAAG

-7743  TAGGGGTGTC AAGAGAGCTG GCATCCCAC AGAGCTGCAC AAGATGACGC GGACAGAG

-7683  TGACACAGGG CTCAGGGCTT CAGACGGGTC GGGAGGCTCA GCTGAGAGTT CAGGGACA
```

Fig.6 (5/11)

```
-7623  CCTGAGGAGC CTCAGTGGGA AAAGAAGCAC TGAAGTGGGA AGTTCTGGAA TGTTCTGG
-7563  AAGCCTGAGT GCTCTAAGGA AATGCTCCCA CCCCGATGTA GCCTGCAGCA CTGGACGG
-7503  TGTGTACCTC CCCGCTGCCC ATCCTCTCAC AGCCCCCGCC TCTAGGGACA CAACTCCT
-7443  CCTAACATGC ATCTTTCCTG TCTCATTCCA CACAAAGGG CCTCTGGGGT CCCTGTTC
-7383  CATTGCAAGG AGTGGAGGTC ACGTTCCCAC AGACCACCCA GCAACAGGGT CCTATGGA
-7323  TGCGGTCAGG AGGATCACAC GTCCCCCAT GCCCAGGGGA CTGACTCTGG GGGTGATG
-7263  TTGGCCTGGA GGCCACTGGT CCCCTCTGTC CCTGAGGGGA ATCTGCACCC TGGAGGCT
-7203  CACATCCCTC CTGATTCTTT CAGCTGAGGG CCCTTCTTGA AATCCCAGGG AGGACTCA
-7143  CCCCACTGGG AAAGGCCCAG TGTGGACGGT TCCACAGCAG CCCAGCTAAG GCCCTTGG
-7083  ACAGATCCTG AGTGAGAGAA CCTTTAGGGA CACAGGTGCA CGGCCATGTC CCCAGTGC
-7023  ACACAGAGCA GGGGCATCTG GACCCTGAGT GTGTAGCTCC CGCGACTGAA CCCAGCCC
-6963  CCCCAATGAC GTGACCCCTG GGTGGCTCC AGGTCTCCAG TCCATGCCAC CAAAATCT
-6903  AGATTGAGGG TCCTCCCTTG AGTCCCTGAT GCCTGTCCAG GAGCTGCCCC CTGAGCAA
-6843  CTAGAGTGCA GAGGGCTGGG ATTGTGGCAG TAAAAGCAGC CACATTTGTC TCAGGAAG
-6783  AAGGGAGGAC ATGAGCTCCA GGAAGGGCGA TGGCGTCCTC TAGTGGGCGC CTCCTGTT
-6723  TGAGCAAAAA GGGGCCAGGA GAGTTGAGAG ATCAGGGCTG GCCTTGGACT AAGGCTCA
-6663  TGGAGAGGAC TGAGGTGCAA AGAGGGGGCT GAAGTAGGGG AGTGGTCGGG AGAGATGG
-6603  GGAGCAGGTA AGGGGAAGCC CCAGGGAGGC CGGGGGAGGG TACAGCAGAG CTCTCCAC
-6543  CTCAGCATTG ACATTTGGGG TGGTCGTGCT AGTGGGGTTC TGTAAGTTGT AGGGTGTT
-6483  GCACCATCTG GGGACTCTAC CCACTAAATG CCAGCAGGAC TCCCTCCCCA AGCTCTAA
-6423  ACCAACAATG TCTCCAGACT TTCCAAATGT CCCCTGGAGA GCAAAATTGC TTCTGGCA
-6363  ATCACTGATC TACGTCAGTC TCTAAAAGTG ACTCATCAGC GAAATCCTTC ACCTCTTG
-6303  AGAAGAATCA CAAGTGTGAG AGGGGTAGAA ACTGCAGACT TCAAAATCTT TCCAAAAG
```

Fig.6 (6/11)

```
-6243  TTTTACTTAA TCAGCAGTTT GATGTCCCAG GAGAAGATAC ATTTAGAGTG TTTAGAGT
-6183  ATGCCACATG GCTGCCTGTA CCTCACAGCA GGAGCAGAGT GGGTTTTCCA AGGGCCTG
-6123  ACCACAACTG GAATGACACT CACTGGGTTA CATTACAAAG TGGAATGTGG GGAATTCT
-6063  AGACTTTGGG AAGGGAAATG TATGACGTGA GCCCACAGCC TAAGGCAGTG GACAGTCC
-6003  TTTGAGGCTC TCACCATCTA GGAGACATCT CAGCCATGAA CATAGCCACA TCTGTCAT
-5943  GAAAACATGT TTTATTAAGA GGAAAAATCT AGGCTAGAAG TGCTTTATGC TCTTTTTT
-5883  CTTTATGTTC AAATTCATAT ACTTTAGAT CATTCCTTAA AGAAGAATCT ATCCCCCT
-5823  GTAAATGTTA TCACTGACTG GATAGTGTTG GTGTCTCACT CCCAACCCCT GTGTGGTG
-5763  AGTGCCCTGC TTCCCCAGCC CTGGGCCCTC TCTGATTCCT GAGAGCTTTG GGTGCTCC
-5703  CATTAGGAGG AAGAGAGGAA GGGTGTTTTT AATATTCTCA CCATTCACCC ATCCACCT
-5643  TAGACACTGG GAAGAATCAG TTGCCCACTC TTGGATTTGA TCCTCGAATT AATGACCT
-5583  ATTTCTGTCC CTTGTCCATT TCAACAATGT GACAGGCCTA AGAGGTGCCT TCTCCATG
-5523  ATTTTTGAGG AGAAGGTTCT CAAGATAAGT TTTCTCACAC CTCTTTGAAT TACCTCCA
-5463  TGTGTCCCCA TCACCATTAC CAGCAGCATT TGGACCCTTT TTCTGTTAGT CAGATGCT
-5403  CCACCTCTTG AGGGTGTATA CTGTATGCTC TCTACACAGG AATATGCAGA GGAAATAG
-5343  AAAGGGAAAT CGCATTACTA TTCAGAGAGA AGAAGACCTT TATGTGAATG AATGAGAG
-5283  TAAAATCCTA AGAGAGCCCA TATAAAATTA TTACCAGTGC TAAAACTACA AAAGTTAC
-5223  TAACAGTAAA CTAGAATAAT AAAACATGCA TCACAGTTGC TGGTAAAGCT AAATCAGA
-5163  TTTTTTTCTT AGAAAAGCA TTCCATGTGT GTTGCAGTGA TGACAGGAGT GCCCTTCA
-5103  CAATATGCTG CCTGTAATTT TTGTTCCCTG GCAGAATGTA TTGTCTTTTC TCCCTTTA
-5043  TCTTAAATGC AAAACTAAAG GCAGCTCCTG GCCCCCTCC CCAAAGTCAG CTGCCTGC
-4983  CCAGCCCCAC GAAGAGCAGA GGCCTGAGCT TCCCTGGTCA AAATAGGGGG CTAGGGAG
-4923  TAACCTTGCT CGATAAAGCT GTGTTCCCAG AATGTCGCTC CTGTTCCCAG GGGCACCA
```

```
-4863  CTGGAGGGTG GTGAGCCTCA CTGGTGGCCT GATGCTTACC TTGTGCCCTC ACACCAGT
-4803  TCACTGGAAC CTTGAACACT TGGCTGTCGC CCGGATCTGC AGATGTCAAG AACTTCTG
-4743  AGTCAAATTA CTGCCCACTT CTCCAGGGCA GATACCTGTG AACATCCAAA ACCATGCC
-4683  AGAACCCTGC CTGGGGTCTA CAACACATAT GGACTGTGAG CACCAAGTCC AGCCCTGA
-4623  CTGTGACCAC CTGCCAAGAT GCCCCTAACT GGGATCCACC AATCACTGCA CATGGCAG
-4563  AGCGAGGCTT GGAGGTGCTT CGCCACAAGG CAGCCCCAAT TTGCTGGGAG TTTCTTGG
-4503  CCTGGTAGTG GTGAGGAGCC TTGGGACCCT CAGGATTACT CCCCTTAAGC ATAGTGGG
-4443  CCCTTCTGCA TCCCCAGCAG GTGCCCCGCT CTTCAGAGCC TCTCTCTCTG AGGTTTAC
-4383  AGACCCCTGC ACCAATGAGA CCATGCTGAA GCCTCAGAGA GAGAGATGGA GCTTTGAC
-4323  GGAGCCGCTC TTCCTTGAGG GCCAGGGCAG GGAAAGCAGG AGGCAGCACC AGGAGTGG
-4263  ACACCAGTGT CTAAGCCCCT GATGAGAACA GGGTGGTCTC TCCCATATGC CCATACCA
-4203  CCTGTGAACA GAATCCTCCT TCTGCAGTGA CAATGTCTGA GAGGACGACA TGTTTCCC
-4143  CCTAACGTGC AGCCATGCCC ATCTACCCAC TGCCTACTGC AGGACAGCAC CAACCCAG
-4083  GCTGGGAAGC TGGGAGAAGA CATGGAATAC CCATGGCTTC TCACCTTCCT CCAGTCCA
-4023  GGGCACCATT TATGCCTAGG ACACCCACCT GCCGGCCCCA GGCTCTTAAG AGTTAGGT
-3963  CCTAGGTGCC TCTGGGAGGC CGAGGCAGGA GAATTGCTTG AACCCGGGAG GCAGAGGT
-3903  CAGTGAGCCG AGATCACACC ACTGCACTCC AGCCTGGGTG ACAGAATGAG ACTCTGTC
-3843  AAAAAAAAAG AGAAAGATAG CATCAGTGGC TACCAAGGGC TAGGGGCAGG GGAAGGTG
-3783  GAGTTAATGA TTAATAGTAT GAAGTTTCTA TGTGAGATGA TGAAAATGTT CTGGAAAA
-3723  AAATATAGTG GTGAGGATGT AGAATATTGT GAATATAATT AACGGCATTT AATTGTAC
-3663  TTAACATGAT TAATGTGGCA TATTTATCT TATGTATTTG ACTACATCCA AGAAACAC
-3603  GGAGAGGGAA AGCCCACCAT GTAAAATACA CCCACCCTAA TCAGATAGTC CTCATTGT
-3543  CCAGGTACAG GCCCCTCATG ACCTGCACAG GAATAACTAA GGATTTAAGG ACATGAGG
```

*Fig. 6 (8/11)*

```
-3483  TCCCAGCCAA CTGCAGGTGC ACAACATAAA TGTATCTGCA AACAGACTGA GAGTAAAG

-3423  GGGGGCACAA ACCTCAGCAC TGCCAGGACA CACACCCTTC TCGTGGATTC TGACTTTA

-3363  TGACCCGGCC CACTGTCCAG ATCTTGTTGT GGGATTGGGA CAAGGGAGGT CATAAAGC

-3303  GTCCCCAGGG CACTCTGTGT GAGCACACGA GACCTCCCCA CCCCCCCACC GTTAGGTC

-3243  CACACATAGA TCTGACCATT AGGCATTGTG AGGAGGACTC TAGCGCGGGC TCAGGGAT

-3183  CACCAGAGAA TCAGGTACAG AGAGGAAGAC GGGGCTCGAG GAGCTGATGG ATGACACA

-3123  GCAGGGTTCC TGCAGTCCAC AGGTCCAGCT CACCCTGGTG TAGGTGCCCC ATCCCCCT

-3063  TCCAGGCATC CCTGACACAG CTCCCTCCCG GAGCCTCCTC CCAGGTGACA CATCAGGG

-3003  CCTCACTCAA GCTGTCCAGA GAGGGCAGCA CCTTGGACAG CGCCCACCCC ACTTCACT

-2943  TCCTCCCTCA CAGGGCTCAG GGCTCAGGGC TCAAGTCTCA GAACAAATGG CAGAGGCC

-2883  TGAGCCCAGA GATGGTGACA GGGCAATGAT CCAGGGGCAG CTGCCTGAAA CGGGAGCA

-2823  TGAAGCCACA GATGGGAGAA GATGGTTCAG GAAGAAAAAT CCAGGAATGG GCAGGAGA

-2763  AGAGGAGGAC ACAGGCTCTG TGGGGCTGCA GCCCAGGATG GGACTAAGTG TGAAGACA

-2703  TCAGCAGGTG AGGCCAGGTC CCATGAACAG AGAAGCAGCT CCCACCTCCC CTGATGCA

-2643  GACACACAGA GTGTGTGGTG CTGTGCCCCC AGAGTCGGGC TCTCCTGTTC TGGTCCCC

-2583  GGAGTGAGAA GTGAGGTTGA CTTGTCCCTG CTCCTCTCTG CTACCCCAAC ATTCACCT

-2523  TCCTCATGCC CCTCTCTCTC AAATATGATT TGGATCTATG TCCCCGCCCA AATCTCAT

-2463  CAAATTGTAA ACCCCAATGT TGGAGGTGGG GCCTTGTGAG AAGTGATTGG ATAATGCG

-2403  TGGATTTTCT GCTTTGATGC TGTTTCTGTG ATAGAGATCT CACATGATCT GGTTGTTT

-2343  AAGTGTGTAG CACCTCTCCC CTCTCTCTCT CTCTCTCTTA CTCATGCTCT GCCATGTA

-2283  ACGTTCCTGT TTCCCCTTCA CCGTCCAGAA TGATTGTAAG TTTTCTGAGG CCTCCCCA

-2223  AGCAGAAGCC ACTATGCTTC CTGTACAACT GCAGAATGAT GAGCGAATTA AACCTCTT

-2163  CTTTATAAAT TACCCAGTCT CAGGTATTTC TTTATAGCAA TGCGAGGACA GACTAATA
```

Fig. 6 (9/11)

```
-2103  ATCTTCTACT CCCAGATCCC CGCACACGCT TAGCCCCAGA CATCACTGCC CCTGGGAG
-2043  TGCACAGCGC AGCCTCCTGC CGACAAAAGC AAAGTCACAA AAGGTGACAA AAATCTGC
-1983  TTGGGGACAT CTGATTGTGA AAGAGGGAGG ACAGTACACT TGTAGCCACA GAGACTGG
-1923  CTCACCGAGC TGAAACCTGG TAGCACTTTG GCATAACATG TGCATGACCC GTGTTCAA
-1863  TCTAGAGATC AGTGTTGAGT AAAACAGCCT GGTCTGGGGC CGCTGCTGTC CCCACTTC
-1803  TCCTGTCCAC CAGAGGGCGG CAGAGTTCCT CCCACCCTGG AGCCTCCCCA GGGGCTGC
-1743  ACCTCCCTCA GCCGGGCCCA CAGCCCAGCA GGGTCCACCC TCACCCGGGT CACCTCGG
-1683  CACGTCCTCC TCGCCCTCCG AGCTCCTCAC ACGGACTCTG TCAGCTCCTC CCTGCAGC
-1623  ATCGGCCGCC CACCTGAGGC TTGTCGGCCG CCCACTTGAG GCCTGTCGGC TGCCCTCT
-1563  AGGCAGCTCC TGTCCCCTAC ACCCCCTCCT TCCCCGGGCT CAGCTGAAAG GGCGTCTC
-1503  AGGGCAGCTC CCTGTGATCT CCAGGACAGC TCAGTCTCTC ACAGGCTCCG ACGCCCCC
-1443  TGCTGTCACC TCACAGCCCT GTCATTACCA TTAACTCCTC AGTCCATGA AGTTCACT
-1383  GCGCCTGTCT CCCGGTTACA GGAAAACTCT GTGACAGGGA CCACGTCTGT CCTGCTCT
-1323  GTGGAATCCC AGGGCCCAGC CCAGTGCCTG ACACGGAACA GATGCTCCAT AAATACTG
-1263  TAAATGTGTG GGAGATCTCT AAAAAGAAGC ATATCACCTC CGTGTGGCCC CCAGCAGT
-1203  GAGTCTGTTC CATGTGGACA CAGGGGCACT GGCACCAGCA TGGGAGGAGG CCAGCAAG
-1143  CCCGCGGCTG CCCCAGGAAT GAGGCCTCAA CCCCCAGAGC TTCAGAAGGG AGGACAGA
-1083  CCTGCAGGGA ATAGATCCTC CGGCCTGACC CTGCAGCCTA ATCCAGAGTT CAGGGTCA
-1023  TCACACCACG TCGACCCTGG TCAGCATCCC TAGGGCAGTT CCAGACAAGG CCGGAGGT
 -963  CCTCTTGCCC TCCAGGGGGT GACATTGCAC ACAGACATCA CTCAGGAAAC GGATTCCC
 -903  GGACAGGAAC CTGGCTTTGC TAAGGAAGTG GAGGTGGAGC CTGGTTTCCA TCCCTTGC
 -843  CAACAGACCC TTCTGATCTC TCCCACATAC CTGCTCTGTT CCTTTCTGGG TCCTATGA
 -783  ACCCTGTTCT GCCAGGGGTC CCTGTGCAAC TCCAGACTCC CTCCTGGTAC CACCATGG
```

Fig. 6 (10/11)

```
-723  AAGGTGGGGT GATCACAGGA CAGTCAGCCT CGCAGAGACA GAGACCACCC AGGACTGT
-663  GGGAGAACAT GGACAGGCCC TGAGCCGCAG CTCAGCCAAC AGACACGGAG AGGGAGGG
-603  CCCCTGGAGC CTTCCCCAAG GACAGCAGAG CCCAGAGTCA CCCACCTCCC TCCACCAC
-543  TCCTCTCTTT CCAGGACACA CAAGACACCT CCCCCTCCAC ATGCAGGATC TGGGGACT
-483  TGAGACCTCT GGGCCTGGGT CTCCATCCCT GGGTCAGTGG CGGGGTTGGT GGTACTGG
-423  ACAGAGGGCT GGTCCCTCCC CAGCCACCAC CCAGTGAGCC TTTTCTAGC CCCCAGAG
-363  ACCTCTGTCA CCTTCCTGTT GGGCATCATC CCACCTTCCC AGAGCCCTGG AGAGCATG
-303  GAGACCCGGG ACCCTGCTGG GTTTCTCTGT CACAAAGGAA ATAATCCCC CTGGTGTG
-243  AGACCCAAGG ACAGAACACA GCAGAGGTCA GCACTGGGGA AGACAGGTTG TCCTCCCA
-183  GGATGGGGGT CCATCCACCT TGCCGAAAAG ATTTGTCTGA GGAACTGAAA ATAGAAGG
-123  AAAAGAGGA GGGACAAAAG AGGCAGAAAT GAGAGGGGAG GGGACAGAGG ACACCTGA
 -63  AAAGACCACA CCCATGACCC ACGTGATGCT GAGAAGTACT CCTGCCCTAG AAGAGAC
  -3  AGGGCAGAGG GAGGAAGGAC AGCAGACCAG ACAGTCACAG CAGCCTTGAC AAAACGTT
  57  TGGAACTCAA GCTCTTCTCC ACAGAGGAGG ACAGAGCAGA CAGCAGAGAC CATGGAGT
 117  CCCTCGGCCC CTCCCCACAG ATGGTGCATC CCTGGCAGA GGCTCCTGCT CACAGGTG
 177  GGGAGGACAA CCTGGGAGAG GGTGGGAGGA GGGAGCTGGG GTCTCCTGGG TAGGACAG
 237  CTGTGAGACG GACAGAGGGC TCCTGTTGGA GCCTGAATAG GGAAGAGGAC ATCAGAGA
 297  GACAGGAGTC ACACCAGAAA AATCAAATTG AACTGGAATT GGAAAGGGGC AGGAAAAC
 357  CAAGAGTTCT ATTTTCCTAG TTAATTGTCA CTGGCCACTA CGTTTTTAAA AATCATAA
 417  ACTGCATCAG ATGACACTTT AAATAAAAAC ATAACCAGGG CATGAAACAC TGTCCTCA
 477  CGCCTACCGC GGACATTGGA AAATAAGCCC CAGGCTGTGG AGGGCCCTGG GAACCCTC
 537  GAACTCATCC ACAGGAATCT GCAGCCTGTC CCAGGCACTG GGGTGCAACC AAGATC
```

US 6,194,211 B1

TRANSCRIPTIONAL REGULATORY SEQUENCE OF CARCINOEMBRYONIC ANTIGEN FOR EXPRESSION TARGETING

This application is filed pursuant to 35 U.S.C. §371 as a U.S. National Phase Application of International Application No. PCT/GB94/02546 filed Nov. 18, 1994 which is a Continuation In Part of Ser. No. 08/154,712 filed Nov. 19, 1993.

TECHNICAL FIELD

The present invention relates to a transcriptional regulatory sequence useful in gene therapy.

BACKGROUND

Colorectal carcinoma (CRC) is the second most frequent cancer and the second leading cause of cancer-associated deaths in the U.S. and Western Europe. The overall five-year survival rate for patients has not meaningfully improved in the last three decades. Prognosis for the CRC cancer patient is associated with the depth of tumor penetration into the bowel wall, the presence of regional lymph node involvement and, most importantly, the presence of distant metastases. The liver is the most common site for distant metastasis and, in approximately 30% of patients, the sole initial site of tumor recurrence after successful resection of the primary colon cancer. Hepatic metastases are the most common cause of death in the CRC cancer patient.

The treatment of choice for the majority of patients with hepatic CRC metastasis is systemic or regional chemotherapy using 5-fluorouracil (5-FU) alone or in combination with other agents such as leviamasole. However, despite extensive effort, there is still no satisfactory treatment for hepatic CRC metastasis. Systemic single- and combination-agent chemotherapy and radiation are relatively ineffective emphasizing the need for new approaches and therapies for the treatment of the diseases.

A gene therapy approach is being developed for primary and metastatic liver tumors that exploits the transcriptional differences between normal and metastatic cells. This approach involves linking the transcriptional regulatory sequences (TRS) of a tumor associated marker gene to the encoding sequence of an enzyme, typically a non-mammalian enzyme, to create an artificial chimaeric gene that is selectively expressed in cancer cells. The enzyme should be capable of converting a non-toxic prodrug into a cytotoxic or cytostatic drug thereby allowing for selective elimination of metastatic cells.

The principle of this approach has been demonstrated using an alpha-fetoprotein/Varicella Zoster virus thymidine kinase chimaera to target hepatocellular carcinoma with the enzyme metabolically activating the non-toxic prodrug 6-methoxypurine arabinonucleoside ultimately leading to formation of the cytoxic anabolite adenine arabinonucleoside triphosphate (see Huber et al, Proc. Natl. Acad. Sci U.S.A., 88, 8039–8043 (1991) and EP-A-0 415 731).

For the treatment of hepatic metastases of CRC, it is desirable to control the expression of an enzyme with the transcriptional regulatory sequences of a tumor marker associated with such metastases.

CEA is a tumor associated marker that is regulated at the transcriptional level and is expressed by most CRC tumors but is not expressed in normal liver. CEA is widely used as an important diagnostic tool for postoperative surveillance, chemotherapy efficacy determinations, immunolocalisation and immunotherapy. The TRS of CEA are potentially of value in the selective expression of an enzyme in $CEA^+$ tumor cells since there appears to be a very low heterogeneity of CEA within metastatic tumors, perhaps because CEA may have an important functional role in metastasis.

The cloning of the CEA gene has been reported and the promoter localised to a region of 424 nucleotides upstream from the translational start (Schrewe et al, Mol. Cell. Biol., 10, 2738–2748 (1990) but the full TRS was not identified.

SUMMARY

In the work on which the present invention is based, CEA genomic clones have been identified and isolated from the human chromosome 19 genomic library LL19NL01, ATCC number 57766, by standard techniques described hereinafter. The CEA enhancers are especially advantageous for high level expression in CEA-positive cells and no expression in CEA-negative cells.

According to one aspect, the present invention provides a DNA molecule comprising the CEA TRS but without associated CEA coding sequence.

According to another aspect, the present invention provides use of a CEA TRS for and targeting expression of a heterologous enzyme to $CEA^+$ cells. Preferably the enzyme is capable of catalysing the production of an agent cytotoxic or cytostatic to the $CEA^+$ target cells.

As described in more detail hereinafter, the present invention have sequenced a large part of the CEA gene upstream of the coding sequence. As used herein, the term "CEA TRS" means any part of the CEA gene upstream of the coding sequence which has a transcriptional regulatory effect on a heterologous coding sequence operably linked thereto.

Certain parts of the sequence of the CEA gene upstream of the coding sequence have been identified as making significant contributions to the transcriptional regulatory effect, more particularly increasing the level and/or selectivity of transcription. Preferably the CEA TRS includes all or part of the region from about −299b to about +69b, more preferably about −90b to about +69b. Increases in the level of transcription and/or selectivity can also be obtained by including one or more of the following regions: −14.5 kb to −10.6 kb, preferably −13.6 kb to −10.6 kb, and/or −6.1 kb to −3.8 kb. All of the regions referred to above can be included in either orientation and in different combinations. In addition, repeats of these regions may be included, particularly repeats of the −90b to +69b region, containing for example 2,3, 4 or more copies of the region. The base numbering refers to the sequence of FIG. 6. The regions referred to are included in the plasmids described in FIG. 5B.

DETAILED DESCRIPTION

Gene therapy involves the stable integration of new genes into target cells and the expression of those genes, once they are in place, to alter the phenotype of that particular target cell (for review see Anderson, W. F. Science 226, 401–409 (1984) and McCormick, D. Biotechnology 3, 689–693, (1985)). Gene therapy may be beneficial for the treatment of genetic diseases that involves the replacement of one defective or missing enzyme, such as; hypoxanthine-guanine phosphoribosyl transferase in Lesch-Nyhan diseases, purine nucleoside phosphorylase in severe immunodeficiency disease, and adenosine deaminase in severed combined immunodeficiency diseases.

It has now been found that it is possible to selectively arrest the growth of, or kill, mammalian carcinoma cells with prodrugs, i.e. chemical agents capable of selective conversion to cytotoxic (causing cell death) or cytostatic (suppressing cell multiplication and growth) metabolites. This is achieved by the construction of a molecular chimaera comprising a "target tissue-specific" TRS that is selectively activated in target cells, such as cancerous cells, and that controls the expression of a heterologous enzyme. This molecular chimaera may be manipulated via suitable vectors and incorporated into an infective virion. Upon administration of an infective virion containing the molecular chimaera to a host (e.g., mammal or human), the enzyme is selectively expressed in the target cells. Administration of prodrugs (compounds that are selectively metabolised by the enzyme into metabolites that are either further metabolised to or are, in fact, cytotoxic or cytostatic agents) can then result in the production of the cytotoxic or cytostatic agent in situ in the cancer cell. According to the present invention CEA TRS provides the target tissue specificity.

Molecular chimaeras (recombinant molecules comprised of unnatural combinations of genes or sections of genes), and infective virions (complete viral particles capable of infecting appropriate host cells) are well known in the art of molecular biology.

A number of enzyme prodrug combinations may be used for the above purpose, providing the enzyme is capable of selectively activating the administered compound either directly or through an intermediate to a cytostatic or cytotoxic metabolite. The choice of compound will also depend on the enzyme system used, but must be selectively metabolised by the enzyme either directly or indirectly to a cytotoxic or cytostatic metabolite. The term heterologous enzyme, as used herein, refers to an enzyme that is derived from or associated with a species which is different from the host to be treated and which will display the appropriate characteristics of the above mentioned selectivity. In addition, it will also be appreciated that a heterologous enzyme may also refer to an enzyme that is derived from the host to be treated that has been modified to have unique characteristics unnatural to the host.

The enzyme cytosine deaminase (CD) catalyses the deamination of cytosine to uracil. Cytosine deaminase is present in microbes and fungi but absent in higher eukaryotes. This enzyme catalyses the hydrolytic deamination of cytosine and 5-fluorocytosine (5-FC) to uracil and 5-fluorouracil (5-FU), respectively. Since mammalian cells do not express significant amounts of cytosine deaminase, they are incapable of converting 5-FC to the toxic metabolite 5-FU and therefore 5-fluorocytosine is nontoxic to mammalian cells at concentrations which are effective for antimicrobial activity. 5-Fluorouracil is highly toxic to mammalian cells and is widely used as an anticancer agent.

In mammalian cells, some genes are ubiquitously expressed. Most genes, however, are expressed in a temporal and/or tissue-specific manner, or are activated in response to extracellular inducers. For example, certain genes are actively transcribed only at very precise times in ontogeny in specific cell types, or in response to some inducing stimulus. This regulation is mediated in part by the interaction between transcriptional regulatory sequences (for example, promoter and enhancer regulatory DNA sequences), and sequence-specific, DNA-binding transcriptional protein factors.

It has now been found that it is possible to alter certain mammalian cells, e.g. colorectal carcinoma cells, metastatic colorectal carcinoma cells and hepatic colorectal carcinoma cells to selectively express a heterologous enzyme as a hereinbefore defined, e.g. CD. This is achieved by the construction of molecular chimaeras in an expression cassette.

Expression cassettes themselves are well known in the art of molecular biology. Such an expression cassette contains all essential DNA sequences required for expression of the heterologous enzyme in a mammalian cell. For example, a preferred expression cassette will contain a molecular chimaera containing the coding sequence for CD, an appropriate polyadenylation signal for a mammalian gene (i.e., a polyadenylation signal that will function in a mammalian cell), and CEA enhancers and promoter sequences in the correct orientation.

Normally, two DNA sequences are required for the complete and efficient transcriptional regulation of genes that encode messenger RNAs in mammalian cells: promoters and enhancers. Promoters are located immediately upstream (5') from the start site of transcription. Promoter sequences are required for accurate and efficient initiation of transcription. Different gene-specific promoters reveal a common pattern of organisation. A typical promoter includes an AT-rich region called a TATA box (which is located approximately 30 base pairs 5' to the transcription initiation start site) and one or more upstream promoter elements (UPEs). The UPEs are a principle target for the interaction with sequence-specific nuclear transcriptional factors. The activity of promoter sequences is modulated by other sequences called enhancers. The enhancer sequence may be a great distance from the promoter in either an upstream (5') or downstream (3') position. Hence, enhancers operate in an orientation- and position-independent manner. However, based on similar structural organisation and function that may be interchanged, the absolute distinction between promoters and enhancers is somewhat arbitrary. Enhancers increase the rate of transcription from the promoter sequence. It is predominantly the interaction between sequence-specific transcriptional factors with the UPE and enhancer sequences that enable mammalian cells to achieve tissue-specific gene expression. The presence of these transcriptional protein factors (tissue-specific, trans-activating factors) bound to the UPE and enhancers (cis-acting, regulatory sequences) enables other components of the transcriptional machinery, including RNA polymerase, to initiate transcription with tissue-specific selectivity and accuracy.

The transcriptional regulatory sequence for CEA is suitable for targeting expression in colorectal carcinoma, metastatic colorectal carcinoma, and hepatic colorectal metastases, transformed cells of the gastrointestinal tract, lung, breast and other tissues. By placing the expression of the gene encoding CD under the transcriptional control of the CRC-associated marker gene, CEA, the nontoxic compound, 5-FC, can be metabolically activated to 5-FU selectively in CRC cells (for example, hepatic CRC cells). An advantage of this system is that the generated toxic compound, 5-fluorouracil, can diffuse out of the cell in which it was generated and kill adjacent tumor cells which did not incorporate the artificial gene for cytosine deaminase.

In the work on which the present invention is based, CEA genomic clones were identified and isolated from the human chromosome 19 genomic library LL19NL01, ATCC number 57766, by standard techniques described hereinafter. The cloned CEA sequences comprise CEA enhancers in addition to the CEA promoter. The CEA enhancers are especially advantageous for high level expression in CEA-positive cells and no expression in CEA-negative cells.

The present invention further provides a molecular chimaera comprising a CEA TRS and a DNA sequence operatively linked thereto encoding a heterologous enzyme, preferably an enzyme capable of catalysing the production of an agent cytotoxic or cytostatic to the CEA$^+$ cells.

The present invention further provides a molecular chimaera comprising a DNA sequence containing the coding sequence of the gene that codes for a heterologous enzyme under the control of a CEA TRS in an expression cassette.

The present invention further provides in a preferred embodiment a molecular chimaera comprising a CEA TRS which is operatively linked to the coding sequence for the gene encoding a non-mammalian cytosine deaminase (CD). The molecular chimaera comprises a promoter and additionally comprises an enhancer.

In particular, the present invention provides a molecular chimaera comprising a DNA sequence of the coding sequence of the gene coding for the heterologous enzyme, which is preferably CD, additionally including an appropriate polyadenylation sequence, which is linked downstream in a 3' position and in the proper orientation to a CEA TRS. Most preferably the expression cassette also contains an enhancer sequence.

Preferably non-mammalian CD is selected from the group consisting of bacterial, fungal, and yeast cytosine deaminase.

The molecular chimaera of the present invention may be made utilizing standard recombinant DNA techniques.

Another aspect of the invention is the genomic CEA sequence as described by Seq ID1.

The coding sequence of CD and a polyadenylation signal (for example see Seq IDs 1 and 2) are placed in the proper 3' orientation to the essential CEA transcriptional regulatory elements. This molecular chimaera enables the selective expression of CD in cells or tissue that normally express CEA. Expression of the CD gene in mammalian CRC and metastatic CRC (hepatic colorectal carcinoma metastases) will enable nontoxic 5-FC to be selectively metabolised to cytotoxic 5-FU.

Accordingly, in a another aspect of the present invention, there is provided a method of constructing a molecular chimaera comprising linking a DNA sequence encoding a heterologous enzyme gene, e.g. CD, to a CEA TRS.

In particular the present invention provides a method of constructing a molecular chimaera as herein defined, the method comprising ligating a DNA sequence encoding the coding sequence and polyadenylation signal of the gene for a heterologous enzyme (e.g. non-mammalian CD) to a CEA TRS (e.g., promoter sequence and enhancer sequence).

These molecular chimaeras can be delivered to the target tissue or cells by a delivery system. For administration to a host (e.g., mammal or human), it is necessary to provide an efficient in vivo delivery system that stably incorporates the molecular chimaera into the cells. Known methods utilize techniques of calcium phosphate transfection, electroporation, microinjection, liposomal transfer, ballistic barrage, DNA viral infection or retroviral infection. For a review of this subject see Biotechniques 6, No.7, (1988).

The technique of retroviral infection of cells to integrate artificial genes employs retroviral shuttle vectors which are known in the art (Miller A. D., Buttimore C. Mol. Cell. Biol. 6, 2985–2902 (1986). Essentially, retroviral shuttle vectors (retroviruses comprising molecular chimaeras used to deliver and stably integrate the molecular chimaera into the genome of the target cell) are generated using the DNA form of the retrovirus contained in a plasmid. These plasmids also contain sequences necessary for selection and growth in bacteria. Retroviral shuttle vectors are constructed using standard molecular biology techniques well known in the art. Retroviral shuttle vectors have the parental endogenous retroviral genes (e.g., gag, pol and env) removed from the vectors and the DNA sequence of interest is inserted, such as the molecular chimaeras that have been described. The vectors also contain appropriate retroviral regulatory sequences for viral encapsidation, proviral insertion into the target genome, message splicing, termination and polyadenylation. Retroviral shuttle vectors have been derived from the Moloney murine leukaemia virus (Mo-MLV) but it will be appreciated that other retroviruses can be used such as the closely related Moloney murine sarcoma virus. Other DNA viruses may also prove to be useful as delivery systems. The bovine papilloma virus (BPV) replicates extrachromosomally, so that delivery systems based on BPV have the advantage that the delivered gene is maintained in a nonintegrated manner.

Thus according to a further aspect of the present invention there is provided a retroviral shuttle vector comprising the molecular chimaeras as hereinbefore defined.

The advantages of a retroviral-mediated gene transfer system are the high efficiency of the gene delivery to the targeted tissue or cells, sequence specific integration regarding the viral genome (at the 5' and 3' long terminal repeat (LTR) sequences) and little rearrangements of delivered DNA compared to other DNA delivery systems.

Accordingly in a preferred embodiment of the present invention there is provided a retroviral shuttle vector comprising a DNA sequence comprising a 5' viral LTR sequence, a cis-acting psi-encapsidation sequence, a molecular chimaera as hereinbefore defined and a 3' viral LTR sequence.

In a preferred embodiment, and to help eliminate non-tissue-specific expression of the molecular chimaera, the molecular chimaera is placed in opposite transcriptional orientation to the 5' retroviral LTR. In addition, a dominant selectable marker gene may also be included that is transcriptionally driven from the 5' LTR sequence. Such a dominant selectable marker gene may be the bacterial neomycin-resistance gene NEO (aminoglycoside 3' phosphotransferase type II), which confers on eukaryotic cells resistance to the neomycin analogue Geneticin (antibiotic G418 sulphate; registered trademark of GIBCO). The NEO gene aids in the selection of packaging cells that contain these sequences.

The retroviral vector is preferably based on the Moloney murine leukaemia virus but it will be appreciated that other vectors may be used. Vectors containing a NEO gene as a selectable marker have been described, for example, the N2 vector (Eglitis M. A., Kantoff P., Gilboa E., Anderson W. F. Science 230, 1395–1398 (1985)).

A theoretical problem associated with retroviral shuttle vectors is the potential of retroviral long terminal repeat (LTR) regulatory sequences transcriptionally activating a cellular oncogene at the site of integration in the host genome. This problem may be diminished by creating SIN vectors. SIN vectors are self-inactivating vectors that contain a deletion comprising the promoter and enhancer regions in the retroviral LTR. The LTR sequences of SIN vectors do not transcriptionally activate 5' or 3' genomic sequences. The transcriptional inactivation of the viral LTR sequences diminishes insertional activation of adjacent target cell DNA sequences and also aids in the selected expression of the delivered molecular chimaera. SIN vectors are created by removal of approximately 299 bp in the 3' viral LTR sequence (Gilboa E., Eglitis P. A., Kantoff P. W., Anderson W. F. Biotechniques 4, 504–512 (1986)).

Thus preferably the retroviral shuttle vectors of the present invention are SIN vectors.

Since the parental retroviral gag, pol, and env genes have been removed from these shuttle vectors, a helper virus system may be utilised to provide the gag, pol, and env retroviral gene products in trans to package or encapsidate the retroviral vector into an infective virion. This is accomplished by utilising specialised "packaging" cell lines, which are capable of generating infectious, synthetic virus yet are deficient in the ability to produce any detectable wild-type virus. In this way the artificial synthetic virus contains a chimaera of the present invention packaged into synthetic artificial infectious virions free of wild-type helper virus. This is based on the fact that the helper virus that is stably integrated into the packaging cell contains the viral structural genes, but is lacking the psi-site, a cis-acting regulatory sequence which must be contained in the viral genomic RNA molecular for it to be encapsidated into an infectious viral particle.

Accordingly, in a still further aspect of the present invention, there is provided an infective virion comprising a retroviral shuttle vector, as hereinbefore described, said vector being encapsidated within viral proteins to create an artificial, infective, replication-defective, retrovirus.

In a another aspect of the present invention there is provided a method for producing infective virions of the present invention by delivering the artificial retroviral shuttle vector comprising a molecular chimaera of the invention, as hereinbefore described, into a packaging cell line.

The packaging cell line may have stably integrated within it a helper virus lacking a psi-site and other regulatory sequence, as hereinbefore described, or, alternatively, the packaging cell line may be engineered so as to contain helper virus structural genes within its genome. In addition to removal of the psi-site, additional alternations can be made to the helper virus LTR regulatory sequences to ensure that the helper virus is not packaged in virions and is blocked at the level of reverse transcription and viral integration. Alternatively, helper virus structural genes (i.e., gag, pol, and env) may be individually and independently transferred into the packaging line. Since these viral structural genes are separated within the packaging cell's genome, there is little chance of convert recombinations generating wild-type virus.

The present invention also provides a packaging cell line comprising an infective virion, as described hereinbefore, said virion further comprising a retroviral shuttle vector.

The present invention further provides for a packaging cell line comprising a retroviral shuttle vector as described hereinbefore.

In addition to retroviral-mediated gene delivery of the chimeric, artificial, therapeutic gene, other gene delivery systems known to those skilled in the art can be used in accordance with the present invention. These other gene delivery systems include other viral gene delivery systems known in the art, such as the adenovirus delivery systems.

Non-viral delivery systems can be utilized in accordance with the present invention as well. For example, liposomal delivery systems can deliver the therapeutic gene to the tumor site via a liposome. Liposomes can be modified to evade metabolism and/or to have distinct targeting mechanisms associated with them. For example, liposomes which have antibodies incorporated into their structure, such as antibodies to CEA, can have targeting ability to CEA-positive cells. This will increase both the selectivity of the present invention as well as its ability to treat disseminated disease (metastasis).

Another gene delivery system which can be utilized according to the present invention is receptor-mediated delivery, wherein the gene of choice is incorporated into a ligand which recognizes a specific cell receptor. This system can also deliver the gene to a specific cell type. Additional modifications can be made to this receptor-mediated delivery system, such as incorporation of adenovirus components to the gene so that the gene is not degraded by the cellular lysosomal compartment after internalization by the receptor.

The infective virion or the packaging cell line according to the invention may be formulated by techniques well known in the art and may be presented as a formulation (composition) with a pharmaceutically acceptable carrier therefor. Pharmaceutically acceptable carriers, in this instance physiologic aqueous solutions, may comprise liquid medium suitable for use as vehicles to introduce the infective virion into a host. An example of such a carrier is saline. The infective virion or packaging cell line may be a solution or suspension in such a vehicle. Stabilizers and antioxidants and/or other excipients may also be present in such pharmaceutical formulations (compositions), which may be administered to a mammal by any conventional method (e.g., oral or parenteral routes). In particular, the infective virion may be administered by intra-venous or intra-arterial infusion. In the case of treating hepatic metastatic CRC, intra-hepatic arterial infusion may be advantageous. The packaging cell line can be administered directly to the tumor or near the tumor and thereby produce infective virions directly at or near the tumor site.

Accordingly, the present invention provides a pharmaceutical formulation (composition) comprising an infective virion or packaging cell line according to the invention in admixture with a pharmaceutically acceptable carrier.

Additionally, the present invention provides methods of making pharmaceutical formulations (compositions), as herein described, comprising mixing an artificial infective virion, containing a molecular chimaera according to the invention as described hereinbefore, with a pharmaceutically acceptable carrier.

The present invention also provides methods of making pharmaceutical formulations (compositions), as herein described, comprising mixing a packaging cell line, containing an infective virion according to the invention as described hereinbefore, with a pharmaceutically acceptable carrier.

Although any suitable compound that can be selectively converted to a cytotoxic or cytotostatic metabolite by the enzyme cytosine deaminase may be utilised, the preferred compound for use according to the invention is 5-FC, in particular for use in treating colorectal carcinoma (CRC), metastatic colorectal carcinoma, or hepatic CRC metastases. 5-FC, which is non-toxic and is used as an antifungal, is converted by CD into the established cancer therapeutic 5-FU.

Any agent that can protentiate the antitumor effects of 5-FU can also protentiate the antitumor effects of 5-FC since, when used according to the present invention, 5-FC is selectively converted to 5-FU. According to another aspect of the present invention, agents such as leucovorin and levemisol, which can potentiate the antitumor effects of 5-FU, can also be used in combination with 5-FC when 5-FC is used according to the present invention. Other agents which can potentiate the antitumor effects of 5-FU are agents which block the metabolism 5-FU. Examples of such agents are 5-substituted uracil derivatives, for example, 5-ethynyluracil and 5-bromvinyluracil (PCT/GB91/01650 (WO 92/04901); Cancer Research 46, 1094, (1986) which are incorporated herein by reference in their entirety). Therefore, a further aspect of the present invention is the use of an agent which can potentiate the antitumor effects of 5-FU, for example, a 5-substituted uracil derivative such as 5-ethynyluracil or 5-bromvinyluracil in combination with 5-FC when 5-FC is used according to the present invention. The present invention further includes the use of agents which are metabolised in vivo to the corresponding 5-substituted uracil derivatives described hereinbefore (see Biochemical Pharmacology 38, 2885, (1989) which is incorporated herein by reference in its entirety) in combination with 5-FC when 5-FC is used according to the present invention.

5-FC is readily available (e.g., United States Biochemical, Sigma) and well known in the art. Leucovorin and levemisol are also readily available and well known in the art.

Two significant advantages of the enzyme/prodrug combination of cytosine deaminase/5-fluorocytosine and further aspects of the invention are the following:
1. The metabolic conversion of 5-FC by CD produces 5-FC which is the drug of choice in the treatment of many different types of cancers, such as colorectal carcinoma.
2. The 5-FU that is selectively produced in one cancer cell can diffuse out of that cell and be taken up by both non-facilitated diffusion and facilitated diffusion into adjacent cells. This produces a neighbouring cell killing effect. This neighbour cell killing effect alleviates the necessity for delivery of the therapeutic molecular chimera to every tumor cell. Rather, delivery of the molecular chimera to a certain percentage of tumor cells can produce the complete eradication of all tumor cells.

The amounts and precise regimen in treating a mammal will of course be the responsibility of the attendant physician, and will depend on a number of factors including the type of severity of the condition to be treated. However, for hepatic metastatic CRC, an intrahepatic arterial infusion of the artificial infective virion at a titer of between $2 \times 10^5$ and $2 \times 10^7$ colony forming units per ml (CFU/ml) infective virions is suitable for a typical tumour. Total amount of virions infused will be dependent on tumour size and are preferably given in divided doses.

Likewise, the packaging cell line is administered directly to a tumour in an amount of between $2 \times 10^5$ and $2 \times 10^7$ cells. Total amount of packaging cell line infused will be dependent on tumour size and is preferably given in divided doses.

Prodrug treatment—Subsequent to infection with the infective virion, certain cytosine compounds (prodrugs of 5-FU) are converted by CD to cytoxic or cytostatic metabolites (e.g. 5-FC is converted to 5-FU) in target cells. The above mentioned prodrug compounds are administered to the host (e.g. mammal or human) between six hours and ten days, preferably between one and five days, after administration of the infective virion.

The dose of 5-FC to be given will advantageously be in the range 10 to 500 mg kg body weight of recipient per day, preferably 50 to 500 mg per kg bodyweight of recipient per day, more preferably 50 to 250 mg per kg bodyweight of recipient per day, and most preferably 50 to 150 mg per kg body weight of recipient per day. The mode of administration of 5-FC in humans are well known to those skilled in the art. Oral administration and/or constant intravenous infusion of 5-FC anticipated by the instant invention to be preferable.

The doses and mode of administration of leucovorin and levemisol to be used in accordance with the present invention are well known or readily determined by those clinicians skilled in the art of oncology.

The dose and mode of administration of the 5-substituted uracil derivatives can be determined by the skilled oncologist. Preferably, these derivatives are given by intravenous injection or orally at a dose of between 0.01 to 50 mg per kg body weight of the recipient per day, particularly 0.01 to 10 mg per kg body weight per day, and more preferably 0.01 to 0.4 mg per kg bodyweight per day depending on the derivative used. An alternative preferred administration regime is 0.5 to 10 mg per kg body weight of recipient once per week.

The following examples serve to illustrate the present invention but should not be construed as a limitation thereof. In the Examples reference is made to the figures a brief description of which is as follows:

BRIEF DESCRIPTION OF THE DRAWINGS

FIG. 5B: Coordinates for CEA sequence present in several CEA/luciferase clones. CEA sequences were cloned into the multiple cloning region of pGL2-Basic (Promega Corp.) by standard techniques.

FIG. 6: CEA genomic sequence from −14463 to +592, comprising SEQ ID NO:1 and SEQ ID NO:2.

EXAMPLE 1

Figure 1:
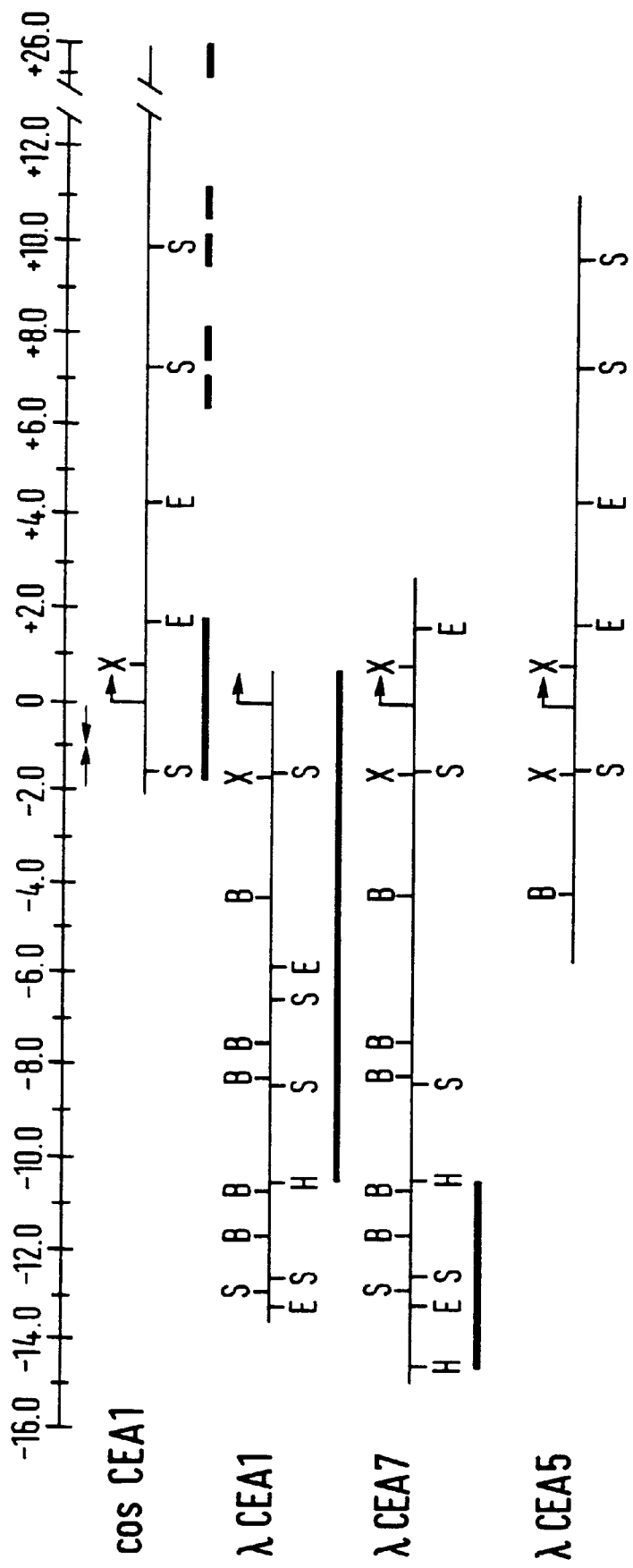
FIG. 1: Diagram of CEA phage clones. The overlapping clones lambdaCEA1, lambdaCEA7, and lambdaCEA5 represent an approximately 26 kb region of CEA genomic sequence. The 11,288 pb HindIII-Sau3A fragment that was sequenced is represented by the heavy line under lambda-CEA1. The 3774 bp HindIII-HindIII fragment that was sequenced is represented by the heavy line under lambda-CEA7. The bent arrows represent the transcription start point for CEA mRNA. The straight arrows represent the oligonucleotides CR15 and CR16. H, HindIII; S. SstI; B, BamHI; E, EcoRI; X, XbaI.

Construction of Transcriptional Regulatory Sequence of Carcinoembryonic Antigen/Cytosine Deaminase Molecular Chimaera A) Cloning and isolation of the transcriptional regulatory sequence of the carcinoembryonic antigen gene CEA genomic clones were identified and isolated from the human chromosome 19 genomic library LL19NL01, ATCC #57766, by standard techniques (Richards et al., Cancer Research, 50, 1521–1527 (1990) which is herein incorporated by reference in its entirety). The CEA clones were identified by plaque hybridization to $^{32}$P end-labelled oligonucleotides CR15 and CR16. CR15, 5'-CCCTGTGATCTCCAGGACAGCTCAGTCTC-3' (SEQ ID NO: 3), and CR16, 5'-GTTTCCTGAGTGATGTCTGTGTGCAATG-3' (SEQ ID NO: 4), hybridize to a 5' non-transcribed region of CEA that has little homology to other members of the CEA gene family. Phage DNA was isolated from three clones that hybridized to both oligonucleotide probes. Polymerase chain reaction, restriction mapping, and DNA sequence analysis confirmed that the three clones contained CEA genomic sequences. The three clones are designated lambdaCEA1, lambdaCEA5, and lambdaCEA7 and have inserts of approximately 13.5, 16.2, and 16.7 kb respectively. A partial restriction map of the three overlapping clones is shown in FIG. 1.

Figure 2:
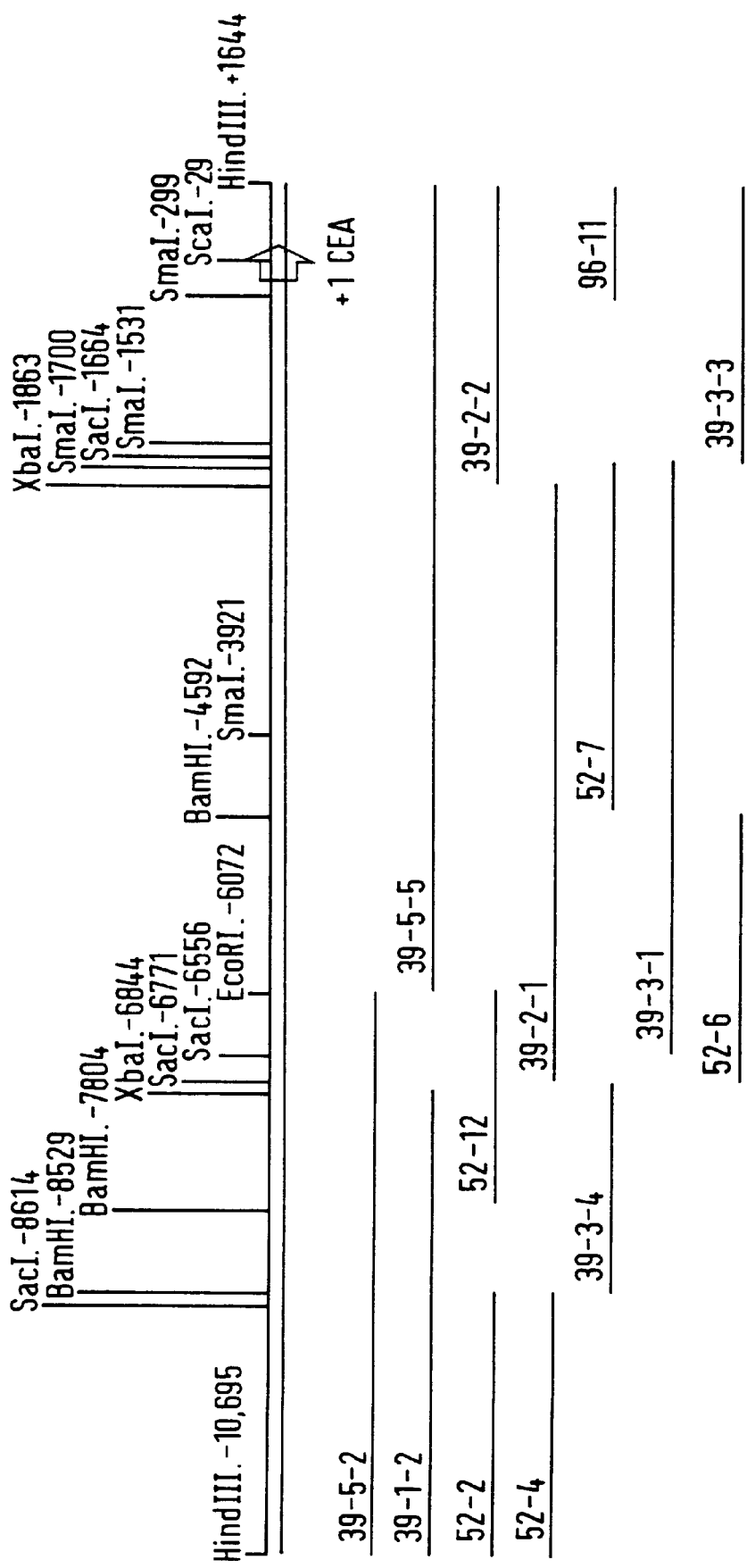
FIG. 2: Restriction map of part of lambdaCEA1. The arrow head represents the approximate location of the transcription imitation point for CEA mRNA. Lines below the map represent the CEA inserts of pBS+ subclones. These subclones are convenient sources for numerous CEA restriction fragments.

Clone lambdaCEA1 was initially chosen for extensive analysis. Fragments isolated from lambdaCEA1 were subcloned using standard techniques into the plasmid pBS+ (Stratagene Cloning Systems, La Jolla, Calif., U.S.A.) to facilitate sequencing, site-directed mutagenesis, and construction of chimeric genes. The inserts of some clones are represented in FIG. 2. The complete DNA sequence of a 11,288 bp HindIII/Sau3A restriction fragment from lambdaCEA1 SEQ ID NO: 1) was determined by the dideoxy sequencing method using the dsDNA Cycle Sequencing System from Life Technologies, Inc. and multiple oligonucleotide primers. This sequence extends from −10.7 kb to +0.6 kb relative to the start site of CEA mRNA. The sequence of 3774 base pair HindIII restriction fragment from lambdaCEA1 was also determined (SEQ ID NO: 2). This sequence extends from −14.5 kb to −10.7 kb relative to the start site of CEA mRNA. This HindIII fragment is present in plasmid pCR145.

To determine important transcriptional regulatory sequences various fragments of CEA genomic DNA are linked to a reporter gene such as luciferase or chloramphenicol acetyltransferase. Various fragments of CEA genomic DNA are tested to determine the optimized, cell-type specific TRS that results in high level reporter gene expression in CEA-positive cells but not in CEA-negative cells. The various reporter constructs, along with appropriate controls, are transfected into tissue culture cell lines that express high, low, or no CEA. The reporter gene analysis identifies both positive and negative transcriptional regulatory sequences. The optimized CEA-specific TRS is identified through the reporter gene analysis and is used to specifically direct the expression of any desired linked coding sequence, such as CD or VZV TK, in cancerous cells that express CEA. The optimized CEA-specific TRS, as used herein, refers to any DNA construct that directs suitably high levels of expression in CEA positive cells and low or no expression in CEA-negative cells. The optimized CEA-specific TRS consists of one or several different fragments of CEA genomic sequence or multimers of selected sequences that are linked together by standard recombinant DNA techniques. It will be appreciated by those skilled in the art that the optimized CEA-specific TRS may also include some sequences that are not derived from the CEA genomic sequences shown in Seq IDs 1 and 2. These other sequences may include sequences from adjoining regions of the CEA locus, such as sequences from the introns, or sequences further upstream or downstream from the sequenced DNA shown in Seq IDs 1 and 2, or they could include transcriptional control elements from other genes that when linked to selected CEA sequences result in the desired CEA-specific regulation.

The CEA sequence of Seq IDs 1 and 2 (FIG. 6) were computer analyzed for characterized consensus sequences which have been associated with gene regulation. Currently not enough is known about transcriptional regulatory sequences to accurately predict by sequence alone whether a sequence will be functional. However, computer searches for characterized consensus sequences can help identify transcriptional regulatory sequences in uncharacterized sequences since many enhancers and promoters consist of unique combinations and spatial alignments of several characterized consensus sequences as well as other sequences. Since not all transcriptional regulatory sequences have been identified and not all sequences that are identical to characterized consensus sequences are functional, such a computer analysis can only suggest possible regions of DNA that may be functionally important for gene regulation.

Figure 3:
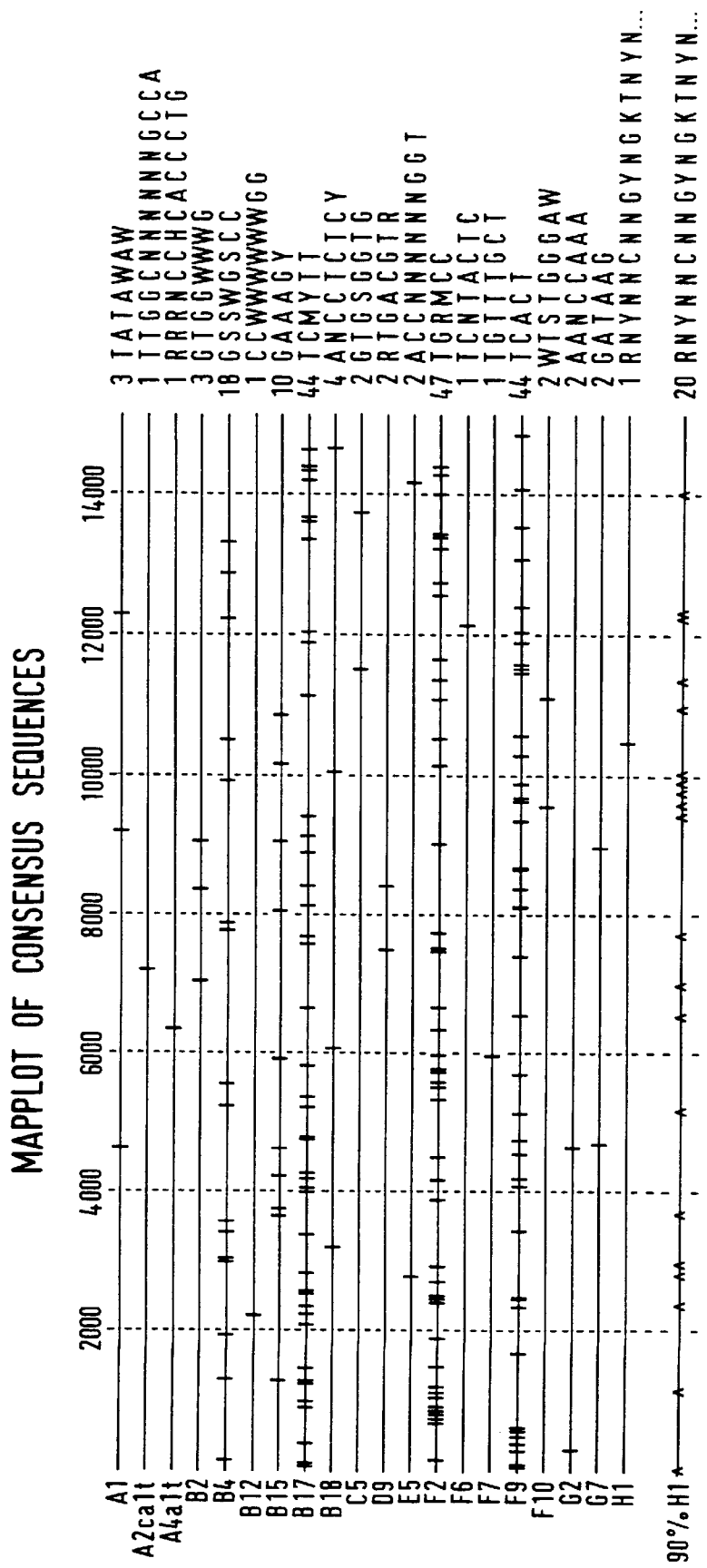
FIG. 3: Mapplot of 15,056 bp HindIII to Sau3A fragment from CEA genomic DNA showing consensus sequences. Schematic representation of some of the consensus sequences found in the CEA sequence of Seq IDs 1 and 2. The consensus sequences shown here are from the transcriptional dictionary of Locker and Buzard (DNA Sequence 1, 3–11 (1980)). The lysozymal silencer is coded B18. The last line represents 90% homology to the topoisomerase II cleavage consensus.

Some examples of the consensus sequences that are present in the CEA sequence are shown in FIG. 3. Four copies of a lysozymal silencer consensus sequences have been found in the CEA sequence. Inclusion of one or more copies of this consensus sequence in the molecular chimera can help optimize CEA-specific expression. A cluster of topoisomerase II cleavage consensus identified approximately 4–5 kb upstream of the CEA transcriptional start suggest that this region of CEA sequence may contain important transcriptional regulatory signals that may help optimize CEA-specific expression.

Figure 4:
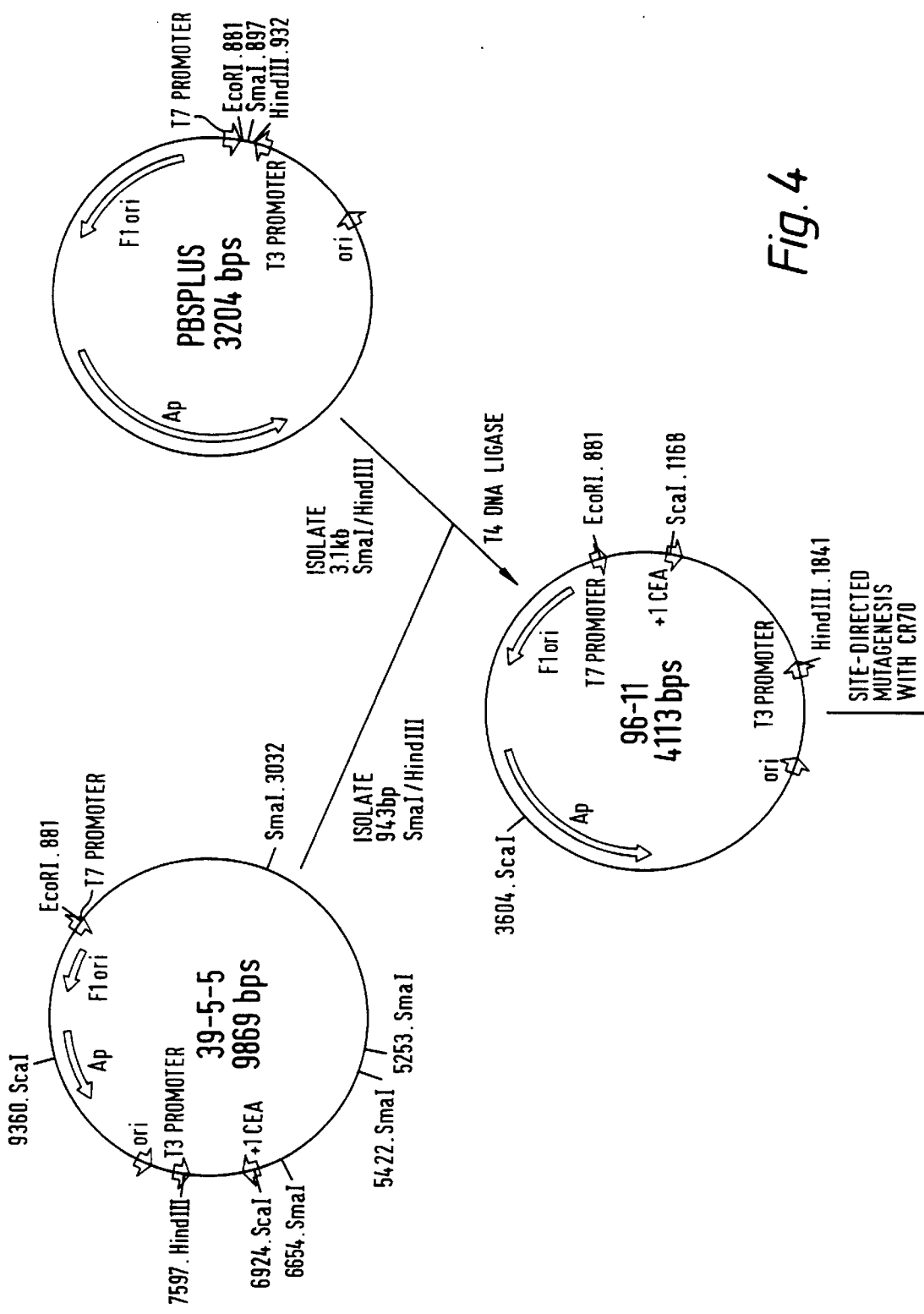
FIG. 4: Cloning scheme for CEA constructs extending from −299 bp to +69 bp.
Figure 4:
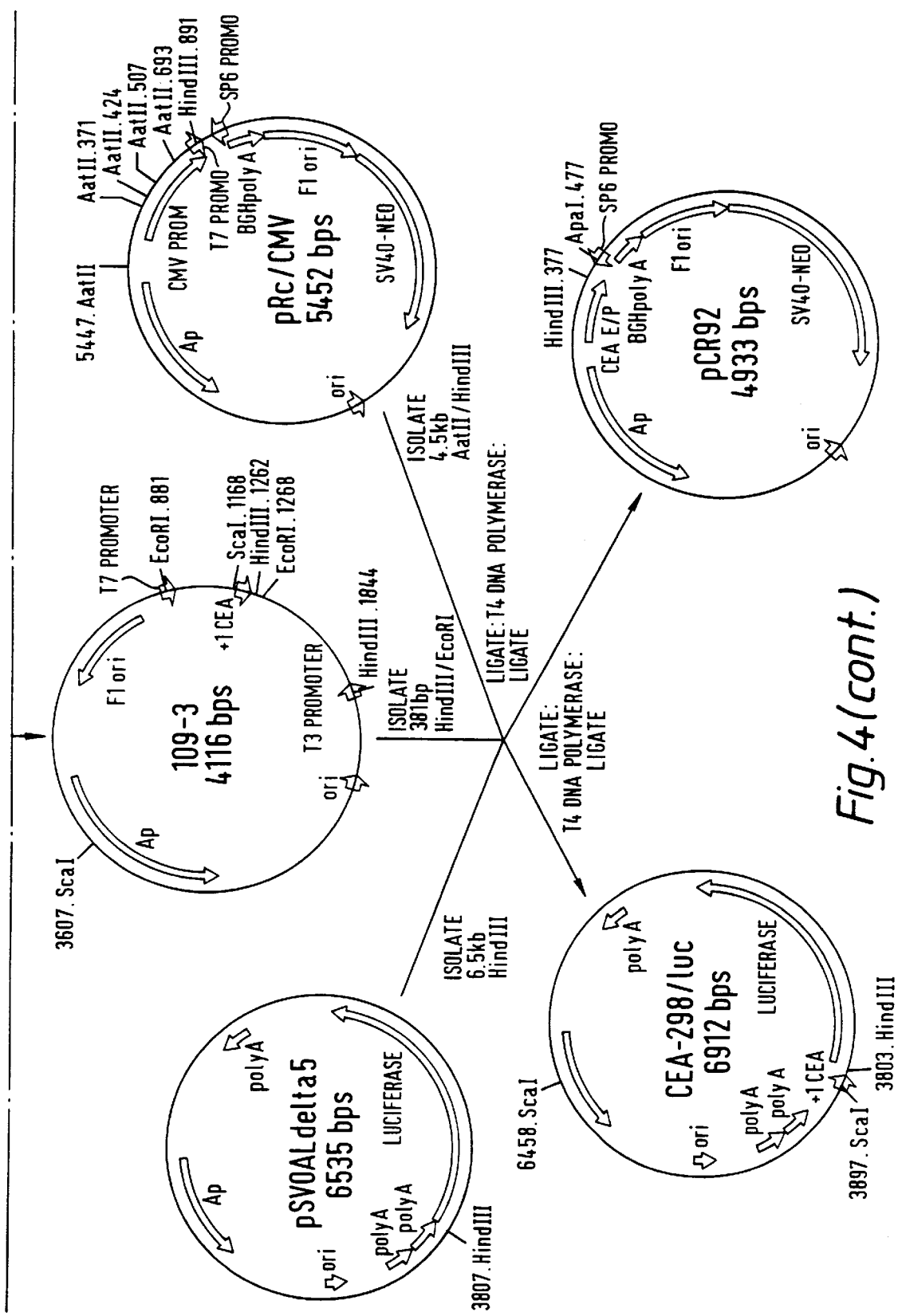

The first fragment of CEA genomic sequence analyzed for transcriptional activity extends from −299 to +69, but it is appreciated by those skilled in the art that other fragments are tested in order to isolate a TRS that directs strong expression in CEA-positive cells but little expression in CEA-negative cells. As diagrammed in FIG. 4 the 943 bp SmaI-HindIII fragment of plasmid 39-5-5 was subcloned into the SmaI-HindIII sites of vector pBS+ (Stategene Cloning Systems) creating plasmid 96-11. Single-stranded DNA was rescued from cultures of XL1-blue 96-11 using an M13 helper virus by standard techniques. Oligonucleotide CR70, 5'-CCTGGAACTCAAGCTTGAATTCTCCA-CAGAGGAGG-3' (SEQ ID NO: 5), was used as a primer for oligonucleotide-directed mutagenesis to introduce HindIII and EcoRI restriction sites at +65. Clone 109-3 was isolated from the mutagenesis reaction and was verified by restriction and DNA sequence analysis to contain the desired changes in the DNA sequence. CEA genomic sequences −299 to +69, original numbering FIG. 3, were isolated from 109-3 as a 381 bp EcoRI/HindIII fragment. Plasmid pRc/CMV (Invitrogen Corporation, San Diego, Calif., U.S.A.) was restricted with AatII and HindIII and the 4.5 kb fragment was isolated from low melting point agarose by standard techniques. The 4.5 kb fragment of pRc/CMV was ligated to the 381 bp fragment of 109-3 using T4 DNA ligase. During this ligation the compatible HindIII ends of the two different restriction fragments were ligated. Subsequently the ligation reaction was supplemented with the four deoxynucleotides, dATP, dCTP, dGTP, and dTTP, and T4 DNA polymerase in order to blunt the non-compatible AatII and EcoRI ends. After incubating, phenol extracting, and ethanol precipitating the reaction, the DNAs were again incubated with T4 DNA ligase. The resulting plasmid, pCR92, allows the insertion of any desired coding sequence into the unique HindIII site downstream of the CEA TRS, upstream from a polyadenylation site and linked to a dominant selectable marker. The coding sequence for CD or other desirable effector or reporter gene, when inserted in the correct orientation into the HindIII site, are transcriptionally regulated by the CEA sequences and are preferably expressed in cells that express CEA but not in cells that do not express CEA.

In order to determine the optimized CEA TRS other reporter gene constructs containing various fragments of CEA genomic sequences are made by standard techniques from DNA isolated from any of the CEA genomic clones (FIGS. 1, 2, 4, and 5). DNA fragments extending from the HindIII site introduced at position +65 (original numbering FIG. 3A) and numerous different upstream sites are isolated and cloned into the unique HindIII site in plasmid p5VOALdelta5' (De Wet, J. R., et al. Mol. Cell. Biol., 7, 725–737 (1987) which is herein incorporated by reference in its entirety) or any similar reporter gene plasmid to construct luciferase reporter gene constructs, FIGS. 4 and 5. These and similar constructs are used in transient expression assays performed in several CEA-positive and CEA-negative cell lines to determine a strong, CEA-positive cell-type specific TRS. FIGS. 5B, 5C, and 5D show the results obtained from several CEA/luciferase reporter constructs. The optimized TRS is used to regulate the expression of CD or other desirable gene in a cell-type specific pattern in order to be able to specifically kill cancer cells. The desirable expression cassette is added to a retroviral shuttle vector to aid in delivery of the expression cassette to cancerous tissue.

Strains containing plasmids 39-5-5 and 39-5-2 were deposited at the ATCC under the Budapest Treaty with Accession No. 68904 and 68905, respectively. A strain containing plasmid pCR92 was deposited with the ATCC under the Budapest Treaty with Accession No. 68914. A strain containing plasmid pCR145 was deposited at the ATCC under the Budapest Treaty with Accession No. 69460.

B) Cloning and isolation of the *E. coli* gene encoding cytosine deaminase (CD)

The cloning, sequencing and expression of *E. coli* CD has already been published (Austin & Huber, Molecular Pharmacology, 43, 380–387 (1993) the disclosure of which is incorporated herein by reference). A positive genetic selection was designed for the cloning of the codA gene from *E. coli*. The selection took advantage of the fact that *E. coli* is only able to metabolize cytosine via CD. Based on this, an *E. coli* strain was constructed that could only utilize cytosine as a pyrimidine source when cytosine deaminase was provided in trans. This strain, BA101, contains a deletion of the codAB operon and a mutation in the pyrF gene. The strain was created by transducing a pyrF mutation (obtained from the *E. coli* strain X82 (*E. coli* Genetic Stock Center, New Haven, Conn., U.S.A.)) into the strain MBM7007 (W. Dallas, Burroughs Wellcome Co., NC, U.S.A.) which carried a deletion of the chromosome from lac to argF. The pyrF mutation confers a pyrimidine requirement on the strain, BA101. In addition, the strain is unable to metabolize cytosine due to the codAB deletion. Thus, BA101 is able to grow on minimal medium supplemented with uracil but is unable to utilize cytosine as the sole pyrimidine source.

The construction of BA101 provided a means for positive selection of DNA fragments encoding. The strain, BA101, was transformed with plasmids carrying inserts from the *E. coli* chromosome and the transformants were selected for growth on minimal medium supplemented with cytosine. Using this approach, the transformants were screened for the ability to metabolize cytosine indicating the presence of a DNA fragment encoding CD. Several sources of DNA could be used for the cloning of the codA gene: 1) a library of the *E. coli* chromosome could be purchased commercially (for example from Clontech, Palo Alto, Calif., U.S.A. or Stratagene, La Jolla, Calif., U.S.A.) and screened; 2) chromosomal DNA could be isolated from *E. coli*, digested with various restriction enzymes and ligated and plasmid DNA with compatible ends before screening; and/or 3) bacteriophage lambda clones containing mapped *E. coli* chromosomal DNA inserts could be screened.

Bacteriophage lambda clones (Y. Kohara, National Institute of Genetics, Japan) containing DNA inserts spanning the 6–8 minute region of the *E. coli* chromosome were screened for the ability to provide transient complementation of the codA defect. Two clones, 137 and 138 were identified in this manner. Large-scale preparations of DNA from these clones were isolated from 500 ml cultures. Restriction enzymes were used to generate DNA fragments ranging in size from 10–12 kilobases. The enzymes used were EcoRI, EcoRI and BamHI, and EcoRI and HindIII. DNA fragments of the desired size were isolated from preparative agarose gels by electroelution. The isolated fragments were ligated to pBR322 (Gibco BRL, Gaithersburg, Md., U.S.A.) with compatible ends. The resulting ligation reactions were used to transfer the *E. coli* strain, DH5α (Gibco BRL, Gaithersburg, Md., U.S.A.). This step was used to amplify the recombinant plasmids resulting from the ligation reactions. The plasmid DNA preparations isolated from the ampicillin-resistant DH5α transformants were digested with the appropriate restriction enzymes to verify the presence of insert DNA. The isolated plasmid DNA was used to transform BA101. The transformed cells were selected for resistance to ampicillin and for the ability to metabolize cytosine. Two clones were isolated pEA001 and pEA002. The plasmid pEA001 contains an approximately 10.8 kb EcoRI-BamHI insert while pEA002 contains an approximately 11.5 kb EcoRI-HindIII insert. The isolated plasmids were used to transform BA101 to ensure that the ability to metabolize cytosine was the result of the plasmid and not due to a spontaneous chromosomal mutation.

A physical map of the pEA001 DNA insert was generated using restriction enzymes. Deletion derivatives of pEA001 were constructed based on this restriction map. The resulting plasmids were screened for the ability to allow BA101 to metabolize cytosine. Using this approach, the codA gene was localized to a 4.8 kb EcoRI-BglII fragment. The presence of codA within these inserts was verified by enzymatic assays for CD activity. In addition, cell extracts prepared for enzymatic assay were also examined by polyacrylamide gel electrophoresis. Cell extracts that were positive for enzymatic activity also had a protein band migrating with an apparent molecular weight of 52,000.

The DNA sequence of both strands was determined for a 1634 bp fragment. The sequence determination began at the PstI site and extended to PvuII site thus including the codA coding domain. An open reading frame of 1283 nucleotides was identified. The thirty amino terminal amino acids were confirmed by protein sequencing. Additional internal amino acid sequences were generated from CNBr-digestion of gel-purified CD.

A 200 bp PstI fragment was isolated that spanned the translational start codon of codA. This fragment was cloned into pBS+. Single-stranded DNA was isolated from 30 ml culture and mutanized using a custom oligonucleotide BA22 purchased from Synthecell Inc., Rockville, Md., U.S.A. and the oligonucleotide-directed mutagenesis kit (Amersham, Arlington Heights, Ill., U.S.A.). The base changes result in the introduction of an HindIII restriction enzyme site for joining of CD with CEA TRS and in a translational start codon of ATG rather than GTG. The resulting 90 bp HindIII-PstI fragment is isolated and ligated with the remainder of the cytosine deaminase gene. The chimeric CEA TRS/cytosine deaminase gene is created by ligating the HindIII-PvuII cytosine deaminase-containing DNA fragment with the CEA TRS sequences.

The strain BA101 and the plasmids, pEA001 and pEA003, were deposited with ATCC under the Budapest Treaty with Accession Nos. 55299, 68916, and 68915 respectively.

C) Construction of transcriptional regulatory sequence of carcinoembryonic antigen/cytosine deaminase molecular chimera A 1508 bp HindIII/PvuII fragment containing the coding sequence for cytosine deaminase is isolated from the plasmid containing the full length CD gene of Example 1B that has been altered to contain a HindIII restriction site just 5' of the initiation codon. Plasmid pCR92 contains CEA sequences −299 to +69 immediately 5' to a unique HindIII restriction site and a polyadenylation signal 3' to a unique ApaI restriction site (Example 1A, FIG. 4). pCR92 is linearised with ApaI, the ends are blunted using dNTPs and T4 DNA polymerase, and subsequently digested with HindIII. The pCR92 HindIII/ApaI fragment is ligated to the 1508 bp HindIII/PvuII fragment containing cytosine deaminase. Plasmid pCEA-1/codA, containing CD inserted in the appropriate orientation relative to the CEA TRS and polyadenylation signal is identified by restriction enzyme and DNA sequence analysis.

The optimized CEA-specific TRS, the coding sequence for CD with an ATG translation start, and a suitable polyadenylation signal are joined together using standard molecular biology techniques. The resulting plasmid, containing CD inserted in the appropriate orientation relative to the optimized CEA specific TRS and a polyadenylation signal is identified by restriction enzyme and DNA sequence analysis.

EXAMPLE 2

Construction of a Retroviral Shuttle Vector Construct Containing the Molecular Chimera of Example 1

The retroviral shuttle vector pL-CEA-1/codA is constructed by ligating a suitable restriction fragment containing the optimized CEA TRS/codA molecular chimera including the polyadenylation signal into an appropriate retroviral shuttle vector, such as N2(XM5) linearised at the XhoI site, using standard molecular biology techniques. The retroviral shuttle vector pL-CEA-1/codA is characterized by restriction endonuclease mapping and partial DNA sequencing.

EXAMPLE 3

Virus Production of Retroviral Constructs of Example 3

The retroviral shuttle construct described in Example 2 is placed into an appropriate packaging cell line, such as PA317, by electroporation or infection. Drug resistant colonies, such as those resistant to G418 when using shuttle vectors containing the NEO gene, are single cell cloned by the limiting dilution method, analyzed by Southern blots, and titred in NIH 3T3 cells to identify the highest producer of full-length virus.

EXAMPLE 4

Further Data on the CEA TRS

Figure 5A:
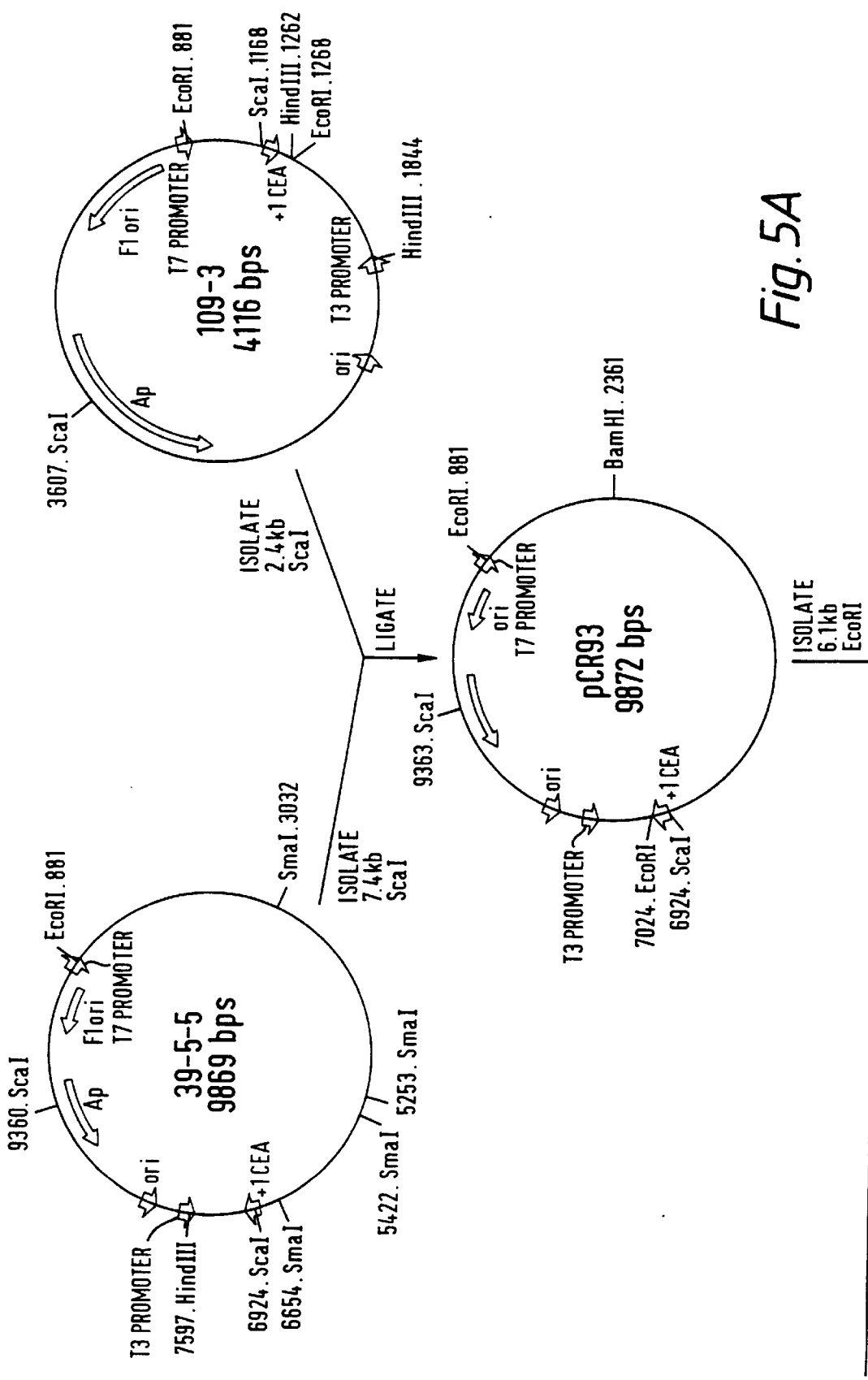
FIG. 5A: Cloning scheme for CEA constructs extending from −10.7 kb to +69 kb.
Figure 5A:
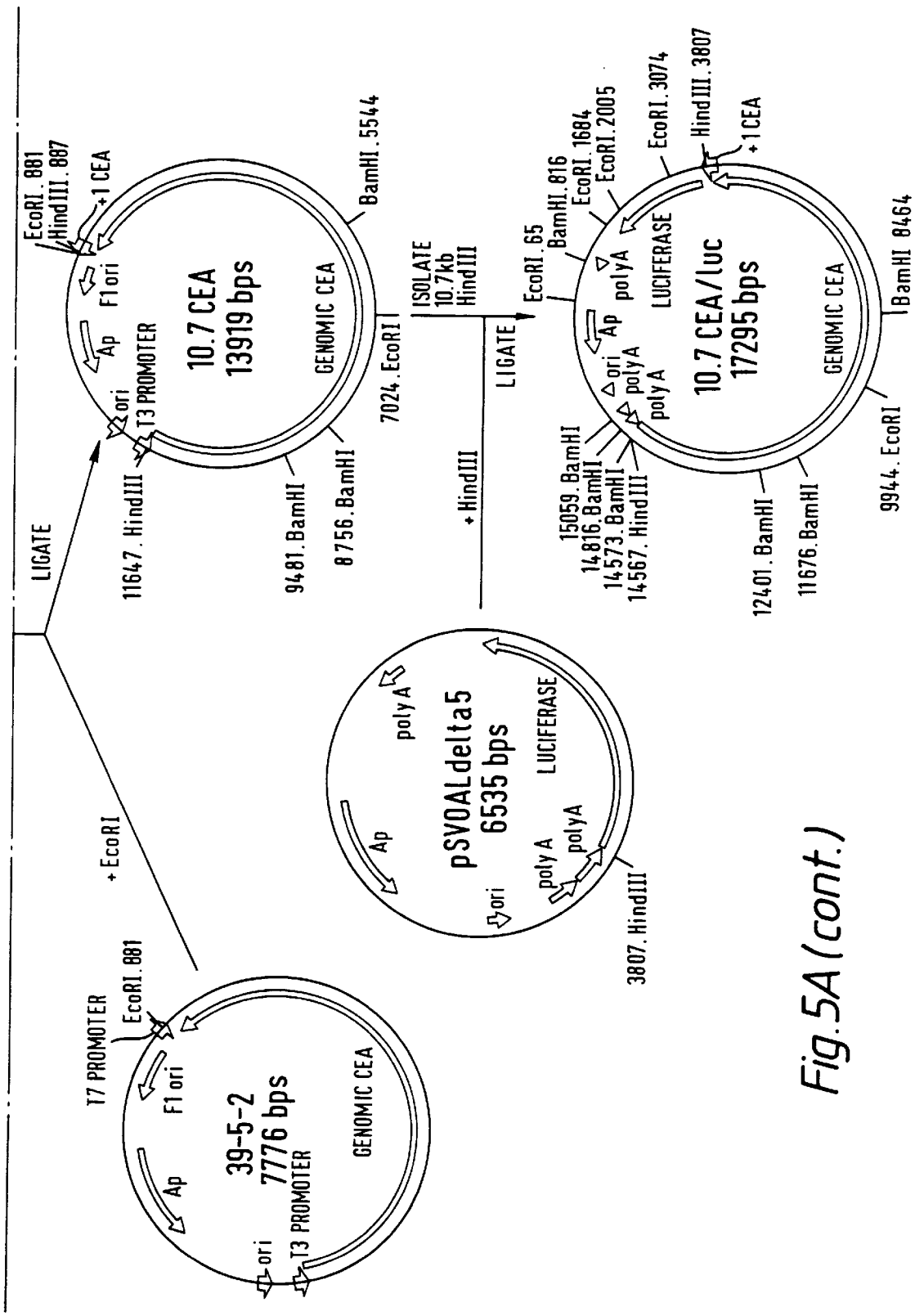
Figure 5C:
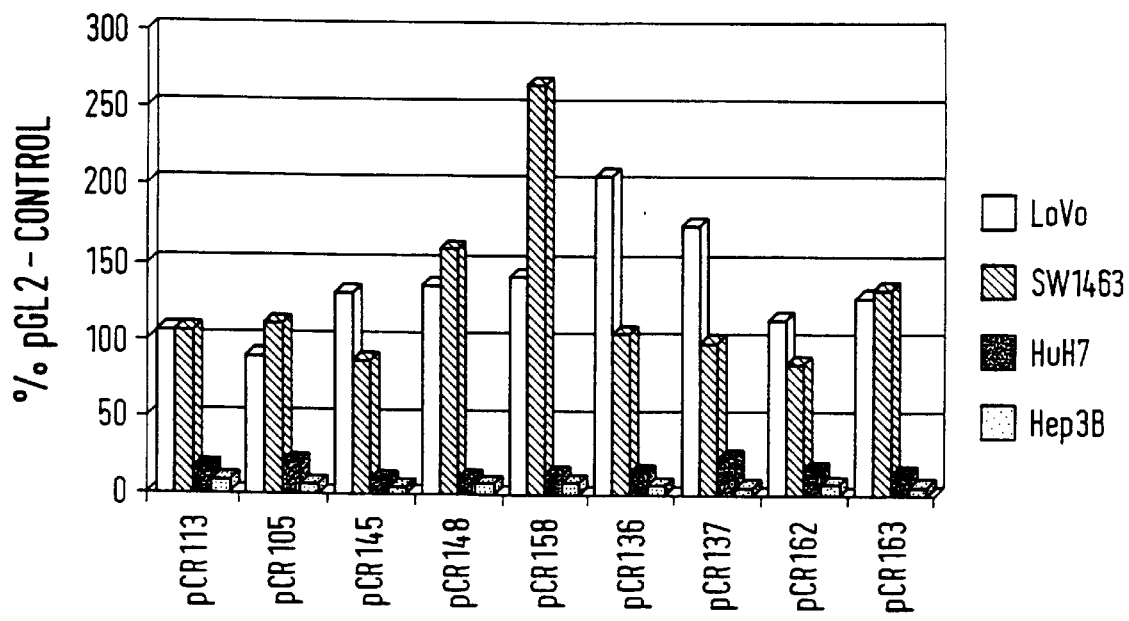
FIGS. 5C and 5D: Transient luciferase assays. Transient transfections and luciferase assays were performed in quadruplicate by standard techniques using DOTAP (Boehringer Mannheim, Indianapolis, Ind., U.S.A.), luciferase assay system (Promega, Madison, Wis., U.S.A.), and Dynatech luminometer (Chantilly, Va., U.S.A.). CEA-positive cell lines included LoVo (ATCC #CCL 229) and SW1463 (ATCC #CCL 234). CEA-negative cells lines included HuH7 and Hep3B (ATCC #HB 8064). C. Luciferase activity expressed as the percent of pGL2-Control plasmid activity. D. Luciferase activities of LoVo and SW1463 expressed as fold increase over activity in Hep3B.
Figure 5D:
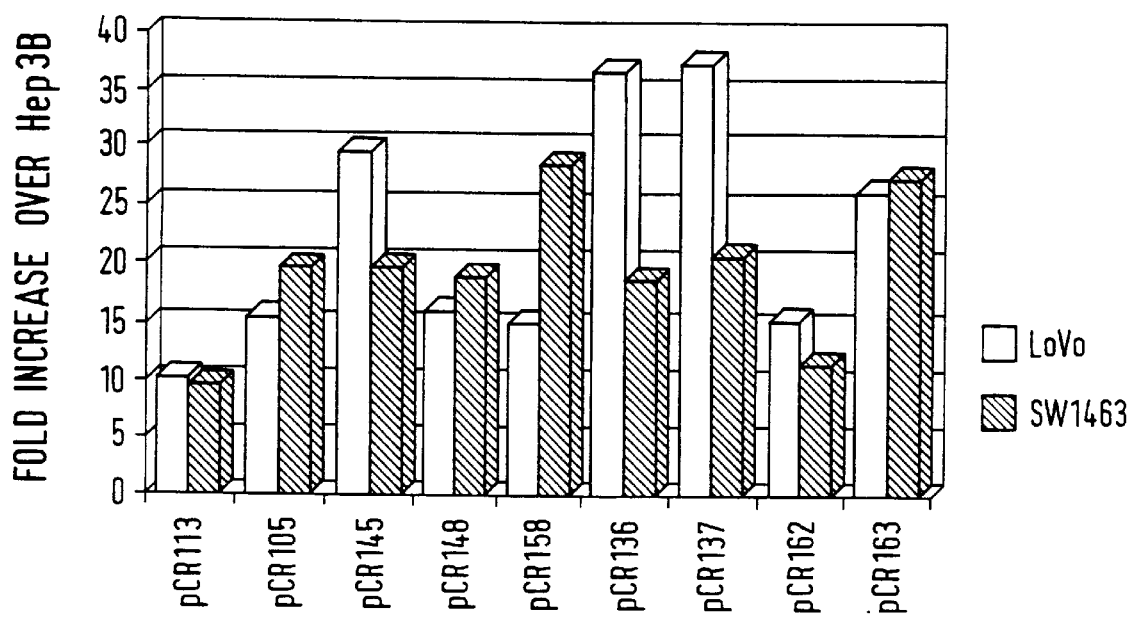

In addition to the plasmids shown in FIG. 5B, the following combinations of regions have proved particularly advantageous at high level expression of the reporter gene in the system described in Example 1A:

pCR177:
(−14.5 kb to −10.6 kb)+(−6.1 kb to −3.9 kb)+(−299b to +69b)
pCR176:
(−13.6 kb to −10.6 kb)+(−6.1 kb to −3.9 kb)+(−299b to +69b)
pCR165:
(−3.9 kb to −6.1 kb)+(4x−90b to +69b)
pCR168:
(−13.6 kb to −10.6 kb)+(4x−90b to +69b).

What is claimed is:

1. A molecular chimera comprising a carcinoembryonic antigen (CEA) transcriptional regulatory sequence (TRS) and a DNA sequence operatively linked thereto encoding a heterologous protein, wherein the CEA TRS comprises:

(a) a CEA promoter element; and (b) a CEA enhancer element comprising a nucleic acid sequence selected from (i) the sequence of FIG. 6 from about −14.4 kb to about −10.6 kb; and (ii) fragments of (i) that act as CEA enhancer elements.

2. A molecular chimera according to claim 1 wherein the heterologous protein is an enzyme capable of catalyzing the production of an agent cytoxic or cytostatic to CEA+ cells.

3. A molecular chimera according to claim 1 to wherein the CEA TRS and the sequence encoding a heterologous protein are in an expression cassette.

4. A retroviral shuttle vector comprising a molecular chimera according to claim 1.

5. A molecular chimera according to claim 1 wherein the CEA promoter element comprises the nucleotide sequence of FIG. 6 from about −90b to about +69b.

6. A molecular chimera according to claim 1 wherein at least one of said CEA TRS elements is in inverse orientation.

7. A molecular chimera according to claim 1 containing multiple copies of said CEA promoter element.

8. A molecular chimera according to claim 1 containing multiple copies of said enhancer element.

9. A molecular chimera according to claim 1 containing at least two different enhancer elements.

10. A molecular chimera according to claim 1 where said DNA encodes an enzyme.

11. The molecular chimera according to claim 2 wherein the heterologous enzyme is cytosine deaminase (CD).

12. A molecular chimera according to claim 3 and additionally comprising an appropriate polyadenylation sequence which is linked downstream in a 3' position to said DNA encoding a heterologous protein, and in proper orientation to the CEA TRS.

13. The retroviral shuttle vector according to claim 4 comprising a DNA sequence comprising a 5' viral LTR sequence, a cis acting psi encapsidation sequence, the molecular chimera and a 3' viral LTR sequence.

14. A retroviral shuttle vector according claim 4 which is a SIN vector.

15. An infective virion comprising a retroviral shuttle vector according to claim 4, the vector being encapsidated within viral proteins to create an artificial, infective, replication defective, retrovirus.

16. A packaging cell line comprising a retroviral shuttle vector according to claim 4.

17. The retroviral shuttle vector according to claim 13 based on Moloney murine leukaemia virus.

18. A composition comprising the infective virion according to claim 15 together with a pharmaceutically acceptable carrier.

19. A composition comprising the packaging cell line according to claim 16 together with a pharmaceutically acceptable carrier.

20. A method of targeting expression of a heterologous protein to CEA+ cells comprising contacting a population of cells that comprises CEA+ cells with said molecular chimera according to claim 1 under conditions such that said molecular chimera enters said cells and expression of said heterologous protein is effected in said CEA+ cells.

21. A molecular chimera comprising a carcinoembryonic antigen (CEA) transcriptional regulatory sequence (TRS) and a DNA sequence operatively linked thereto encoding a heterologous enzyme, wherein the CEA TRS comprises:

a) a CEA promoter element comprising the sequence of from about −90b to about +69b of FIG. 6; and b) an enhancer element, said enhancer element comprising a nucleic acid sequence selected from (i) the sequence of FIG. 6 from about −14.4 kb to about −10.6 kb, and (ii) fragments thereof that act as CEA enhancer elements.

22. A molecular chimera according to claim 21 wherein the heterologous enzyme is capable of catalyzing the production of an agent cytotoxic or cytostatic to CEA+ cells.

23. A molecular chimera according to claim 21 wherein the heterologous enzyme is cytosine deaminase (CD).

24. A retroviral shuttle vector comprising the molecular chimera according to claim 21.

25. A method of targeting expression of a heterologous enzyme to CEA+ cells comprising contacting a population of cells that comprises CEA+ cells with said molecular chimera according to claim 21 under conditions such that said molecular chimera enters said cells and expression of said heterologous enzyme protein is effected in said CEA+ cells.

* * * * *

SEQUENCE LISTING

<160> NUMBER OF SEQ ID NOS: 25

<210> SEQ ID NO 1
<211> LENGTH: 11288
<212> TYPE: DNA
<213> ORGANISM: Homo sapiens

<400> SEQUENCE: 1

```
aagcttaaaa cccaatggat tgacaacatc aagagttgga acaagtggac atggagatgt      60
tacttgtgga aatttagatg tgttcagcta tcgggcagga gaatctgtgt caaattccag     120
catggttcag aagaatcaaa aagtgtcaca gtccaaatgt cgaacagtgc agggggataaa    180
```

```
actgtggtgc attcaaactg agggatattt tggaacatga gaaaggaagg gattgctgct    240
gcacagaaca tggatgatct cacacataga gttgaaagaa aggagtcaat cgcagaatag    300
aaaatgatca ctaattccac ctctataaag tttccaagag gaaaacccaa ttctgctgct    360
agagatcaga atggaggtga cctgtgcctt gcaatggctg tgagggtcac gggagtgtca    420
cttagtgcag gcaatgtgcc gtatcttaat ctgggcaggg cttccatgag cacataggaa    480
tgcagacatt actgctgtgt tcattttact tcaccggaaa agaagaataa aatcagccgg    540
gcgcggtggc tcacgcctgt aatcccagca ctttagaagg ctgaggtggg cagattactt    600
gaggtcagga gttcaagacc accctggcca atatggtgaa accccggctc tactaaaaat    660
acaaaaatta gctgggcatg gtggtgcgcg cctgtaatcc cagctactcg ggaggctgag    720
gctggacaat tgcttggacc caggaagcag aggttgcagt gagccaagat tgtgccactg    780
cactccagct tgggcaacag agccagactc tgtaaaaaaa aaaaaaaaaa aaaaaaaag    840 aaagaaagaa aagaaaaga agtataaaa tctctttggg ttaacaaaa aagatccaca    900 aaacaaacac cagctcttat caaacttaca caactctgcc agagaacagg aaacacaaat    960
actcattaac tcactttgt ggcaataaaa ccttcatgtc aaaggagac caggacacaa    1020 tgaggaagta aaactgcagg ccctacttgg gtgcagagag ggaaaatcca caaataaaac    1080
attaccagaa ggagctaaga tttactgcat tgagttcatt ccccaggtat gcaaggtgat    1140
tttaacacct gaaaatcaat cattgccttt actacataga cagattagct agaaaaaaat    1200
tacaactagc agaacagaag caatttggcc ttcctaaaat tccacatcat atcatcatga    1260
tggagacagt gcagacgcca atgacaataa aaagagggac ctccgtcacc cggtaaacat    1320
gtccacacag ctccagcaag cacccgtctt cccagtgaat cactgtaacc tccccttaa    1380 tcagccccag gcaaggctgc ctgcgatggc cacacaggct ccaacccgtg ggcctcaacc    1440
tcccgcagag gctctccttt ggccacccca tggggagagc atgaggacag gcagagccc    1500 tctgatgccc acacatggca ggagctgacg ccagagccat gggggctgga gagcagagct    1560 gctgggggtca gagcttcctg aggacaccca ggcctaaggg aaggcagctc cctggatggg    1620
ggcaaccagg ctccgggctc caacctcaga gcccgcatgg gaggagccag cactctaggc    1680
cttccctagg gtgactctga ggggaccctg acacgacagg atcgctgaat gcacccgaga    1740
tgaaggggcc accacgggac cctgctctcg tggcagatca ggagagagtg ggacaccatg    1800
ccaggccccc atggcatggc tgcgactgac ccaggccact cccctgcatg catcagcctc    1860
ggtaagtcac atgaccaagc ccaggaccaa tgtggaagga aggaaacagc atccccttta    1920
gtgatggaac ccaaggtcag tgcaaagaga ggccatgagc agttaggaag ggtggtccaa    1980
cctacagcac aaaccatcat ctatcataag tagaagccct gctccatgac ccctgcattt    2040 aaataaaacgt ttgttaaatg agtcaaattc cctcaccatg agagctcacc tgtgtgtagg    2100
cccatcacac acacaaacac acacacacac acacacacac acacagggaa    2160
agtgcaggat cctggacagc accaggcagg cttcacaggc agagcaaaca gcgtgaatga    2220
cccatgcagt gccctgggcc ccatcagctc agagaccctg tgagggctga gatggggcta    2280
ggcaggggag agacttagag agggtgggggc ctccagggag ggggctgcag ggagctgggt    2340
actgccctcc agggagggggg ctgcaggggag ctgggtactg ccctccagggg aggggctgc    2400 agggagctgg gtactgccct ccaggagggg ggctgcaggg agctgggtac tgccctccag    2460
ggagggggct gcaggagct gggtactgcc ctccagggag gcaggagcac tgttcccaac    2520
```

```
agagagcaca tcttcctgca gcagctgcac agacacagga gccccatga ctgccctggg    2580 ccagggtgtg gattccaaat ttcgtgcccc attgggtggg acggaggttg accgtgacat    2640 ccaagggca tctgtgattc caaacttaaa ctactgtgcc tacaaaatag gaaataaccc     2700 tacttttct actatctcaa attccctaag cacaagctag caccctttaa atcaggaagt     2760
tcagtcactc ctggggtcct cccatgcccc cagtctgact tgcaggtgca cagggtggct    2820
gacatctgtc cttgctcctc ctcttggctc aactgccgcc cctcctgggg gtgactgatg    2880
gtcaggacaa gggatcctag agctggcccc atgattgaca ggaaggcagg acttggcctc    2940
cattctgaag actaggggtg tcaagagagc tgggcatccc acagagctgc acaagatgac    3000
gcggacagag ggtgacacag ggctcagggc ttcagacggg tcgggaggct cagctgagag    3060
ttcagggaca gacctgagga gcctcagtgg gaaaagaagc actgaagtgg gaagttctgg    3120
aatgttctgg acaagcctga gtgctctaag gaaatgctcc caccccgatg tagcctgcag    3180
cactggacgg tctgtgtacc tccccgctgc ccatcctctc acagccccg cctctaggga     3240 cacaactcct gccctaacat gcatctttcc tgtctcattc cacacaaaag ggcctctggg    3300
gtccctgttc tgcattgcaa ggagtggagg tcacgttccc acagaccacc cagcaacagg    3360
gtcctatgga ggtgcggtca ggaggatcac acgtccccc atgcccaggg gactgactct     3420
gggggtgatg gattggcctg gaggccactg gtcccctctg tccctgaggg gaatctgcac    3480
cctggaggct gccacatccc tcctgattct ttcagctgag ggcccttctt gaaatcccag    3540
ggaggactca accccactg ggaaaggccc agtgtggacg gttccacagc agcccagcta     3600
aggcccttgg acacagatcc tgagtgagag aacctttagg gacacaggtg cacggccatg    3660
tccccagtgc ccacacagag caggggcatc tggaccctga gtgtgtagct cccgcgactg    3720
aacccagccc ttccccaatg acgtgacccc tggggtggct ccaggtctcc agtccatgcc    3780
accaaaatct ccagattgag ggtcctccct tgagtccctg atgcctgtcc aggagctgcc    3840
ccctgagcaa atctagagtg cagagggctg ggattgtggc agtaaaagca gccacatttg    3900
tctcaggaag gaaagggagg acatgagctc caggaagggc gatggcgtcc tctagtgggc    3960
gcctcctgtt aatgagcaaa aaggggccag gagagttgag agatcagggc tggccttgga    4020
ctaaggctca gatggagagg actgaggtgc aaagagggg ctgaagtagg ggagtggtcg      4080
ggagagatgg gaggagcagg taaggggaag ccccagggag gccgggggag ggtacagcag    4140
agctctccac tcctcagcat tgacatttgg ggtggtcgtg ctagtggggt tctgtaagtt    4200
gtagggtgtt cagcaccatc tggggactct acccactaaa tgccagcagg actccctccc    4260
caagctctaa caaccaacaa tgtctccaga cttcccaaat gtcccctgga gagcaaaatt    4320
gcttctggca gaatcactga tctacgtcag tctctaaaag tgactcatca gcgaaatcct    4380
tcacctcttg ggagaagaat cacaagtgtg agagggtag aaactgcaga cttcaaaatc     4440
tttccaaaag agttttactt aatcagcagt ttgatgtccc aggagaagat acatttagag    4500
tgtttagagt tgatgccaca tggctgcctg tacctcacag caggagcaga gtgggttttc    4560
caagggcctg taaccacaac tggaatgaca ctcactgggt tacattacaa agtggaatgt    4620
ggggaattct gtagactttg ggaagggaaa tgtatgacgt gagcccacag cctaaggcag    4680
tggacagtcc actttgaggc tctcaccatc taggagacat ctcagccatg aacatagcca    4740
catctgtcat tagaaaacat gttttattaa gaggaaaaat ctaggctaga agtgcttttat   4800 gctcttttt ctctttatgt tcaaattcat atactttag atcattcctt aaagaagaat      4860 ctatcccct aagtaaatgt tatcactgac tggatagtgt tggtgtctca ctcccaaccc     4920
```

-continued

```
ctgtgtggtg acagtgccct gcttccccag ccctgggccc tctctgattc ctgagagctt    4980
tgggtgctcc ttcattagga ggaagagagg aagggtgttt ttaatattct caccattcac    5040
ccatccacct cttagacact gggaagaatc agttgcccac tcttggattt gatcctcgaa    5100
ttaatgacct ctatttctgt cccttgtcca tttcaacaat gtgacaggcc taagaggtgc    5160
cttctccatg tgattttga ggagaaggtt ctcaagataa gttttctcac acctctttga    5220
attacctcca cctgtgtccc catcaccatt accagcagca tttggaccct ttttctgtta    5280
gtcagatgct ttccacctct tgagggtgta tactgtatgc tctctacaca ggaatatgca    5340
gaggaaatag aaaaagggaa atcgcattac tattcagaga gaagaagacc tttatgtgaa    5400
tgaatgagag tctaaaatcc taagagagcc catataaaat tattaccagt gctaaaacta    5460
caaaagttac actaacagta aactagaata ataaacatg catcacagtt gctggtaaag    5520
ctaaatcaga tattttttc ttagaaaaag cattccatgt gtgttgcagt gatgacagga    5580
gtgcccttca gtcaatatgc tgcctgtaat ttttgttccc tggcagaatg tattgtcttt    5640 tctccctta aatcttaaat gcaaaactaa aggcagctcc tgggccccct ccccaaagtc    5700
agctgcctgc aaccagcccc acgaagagca gaggcctgag cttccctggt caaaataggg    5760
ggctagggag cttaaccttg ctcgataaag ctgtgttccc agaatgtcgc tcctgttccc    5820
aggggcacca gcctggaggg tggtgagcct cactggtggc ctgatgctta ccttgtgccc    5880
tcacaccagt ggtcactgga accttgaaca cttggctgtc gcccggatct gcagatgtca    5940
agaacttctg gaagtcaaat tactgcccac ttctccaggg cagatacctg tgaacatcca    6000
aaaccatgcc acagaaccct gcctggggtc tacaacacat atggactgtg agcaccaagt    6060
ccagccctga atctgtgacc acctgccaag atgcccctaa ctgggatcca ccaatcactg    6120
cacatggcag gcagcgaggc ttggaggtgc ttcgccacaa ggcagcccca atttgctggg    6180
agtttcttgg cacctggtag tggtgaggag ccttgggacc ctcaggatta ctcccttaa    6240 gcatagtggg gacccttctg catccccagc aggtgccccg ctcttcagag cctctctctc    6300
tgaggtttac ccagacccct gcaccaatga gaccatgctg aagcctcaga gagagagatg    6360
gagctttgac caggagccgc tcttccttga gggccaggc agggaaagca ggaggcagca    6420
ccaggagtgg gaacaccagt gtctaagccc ctgatgagaa cagggtggtc tctcccatat    6480
gcccatacca ggcctgtgaa cagaatcctc cttctgcagt gacaatgtct gagaggacga    6540
catgtttccc agcctaacgt gcagccatgc ccatctaccc actgcctact gcaggacagc    6600
accaacccag gagctgggaa gctgggagaa gacatggaat acccatggct tctcaccttc    6660
ctccagtcca gtgggcacca tttatgccta ggacacccac ctgccggccc caggctctta    6720
agagttaggt cacctaggtg cctctgggag gccgaggcag gagaattgct tgaacccggg    6780
aggcagaggt tgcagtgagc cgagatcaca ccactgcact ccagcctggg tgacagaatg    6840
agactctgtc tcaaaaaaaa agagaaagat agcatcagtg ctaccaagg ctaggggca    6900 ggggaaggtg gagagttaat gattaatagt atgaagtttc tatgtgagat gatgaaaatg    6960
ttctggaaaa aaaatatag tggtgaggat gtagaatatt gtgaatataa ttaacggcat    7020
ttaattgtac acttaacatg attaatgtgg catatttat cttatgtatt tgactacatc    7080
caagaaacac tgggagaggg aaagcccacc atgtaaaata cacccaccct aatcagatag    7140
tcctcattgt acccaggtac aggccccta tgacctgcac aggaataact aaggatttaa    7200
ggacatgagg cttcccagcc aactgcaggt gcacaacata aatgtatctg caaacagact    7260
```

-continued

```
gagagtaaag ctgggggcac aaacctcagc actgccagga cacacaccct tctcgtggat    7320
tctgacttta tctgacccgg cccactgtcc agatcttgtt gtgggattgg acaagggag    7380 gtcataaagc ctgtcccag ggcactctgt gtgagcacac gagacctccc cacccccca    7440 ccgttaggtc tccacacata gatctgacca ttaggcattg tgaggaggac tctagcgcgg    7500
gctcagggat cacaccagag aatcaggtac agagaggaag acgggctcg aggagctgat    7560 ggatgacaca gagcagggtt cctgcagtcc acaggtccag ctcaccctgg tgtaggtgcc    7620 ccatcccct gatccaggca tccctgacac agctccctcc cggagcctcc tcccaggtga    7680
cacatcaggg tccctcactc aagctgtcca gagagggcag caccttggac agcgcccacc    7740
ccacttcact cttcctccct cacagggctc agggctcagg gctcaagtct cagaacaaat    7800
ggcagaggcc agtgagccca gagatggtga cagggcaatg atccaggggc agctgcctga    7860
aacgggagca ggtgaagcca cagatgggag aagatggttc aggaagaaaa atccaggaat    7920
gggcaggaga ggagaggagg acacaggctc tgtgggctg cagcccagga tgggactaag    7980
tgtgaagaca tctcagcagg tgaggccagg tcccatgaac agagaagcag ctcccacctc    8040
ccctgatgca cggacacaca gagtgtgtgg tgctgtgccc ccagagtcgg gctctcctgt    8100
tctggtcccc agggagtgag aagtgaggtt gacttgtccc tgctcctctc tgctacccca    8160
acattcacct tctcctcatg cccctctctc tcaaatatga tttggatcta tgtccccgcc    8220
caaatctcat gtcaaattgt aaaccccaat gttggaggtg gggccttgtg agaagtgatt    8280
ggataatgcg ggtggatttt ctgctttgat gctgtttctg tgatagagat ctcacatgat    8340
ctggttgttt aaaagtgtgt agcacctctc ccctctctct ctctctctct tactcatgct    8400
ctgccatgta agacgttcct gtttccctt caccgtccag aatgattgta agttttctga    8460
ggcctcccca ggagcagaag ccactatgct tcctgtacaa ctgcagaatg atgagcgaat    8520
taaacctctt ttcttataa attacccagt ctcaggtatt tctttatagc aatgcgagga    8580
cagactaata caatcttcta ctcccagatc cccgcacacg cttagcccca gacatcactg    8640
cccctgggag catgcacagc gcagcctcct gccgacaaaa gcaaagtcac aaaaggtgac    8700
aaaaatctgc atttggggac atctgattgt gaaagaggga ggacagtaca cttgtagcca    8760
cagagactgg ggctcaccga gctgaaacct ggtagcactt tggcataaca tgtgcatgac    8820
ccgtgttcaa tgtctagaga tcagtgttga gtaaaacagc ctggtctggg gccgctgctg    8880
tccccacttc cctcctgtcc accagagggc ggcagagttc ctcccaccct ggagcctccc    8940 cagggctgc tgacctccct cagccgggcc cacagcccag caggtccac cctcacccgg    9000 gtcacctcgg cccacgtcct cctcgccctc cgagctcctc acacggactc tgtcagctcc    9060
tccctgcagc ctatcggccg cccacctgag gcttgtcggc cgcccacttg aggcctgtcg    9120
gctgccctct gcaggcagct cctgtcccct acaccccctc cttccccggg ctcagctgaa    9180
agggcgtctc ccagggcagc tccctgtgat ctccaggaca gctcagtctc tcacaggctc    9240
cgacgccccc tatgctgtca cctcacagcc ctgtcattac cattaactcc tcagtcccat    9300
gaagttcact gagcgcctgt ctcccggtta caggaaaact ctgtgacagg gaccacgtct    9360
gtcctgctct ctgtggaatc ccagggccca gcccagtgcc tgacacgaa cagatgctcc    9420 ataaatactg gttaaatgtg tgggagatct ctaaaaagaa gcatatcacc tccgtgtggc    9480
ccccagcagt cagagtctgt tccatgtgga cacaggggca ctggcaccag catgggagga    9540
ggccagcaag tgcccgcggc tgcccccagga atgaggcctc aacccccaga gcttcagaag    9600
ggaggacaga ggcctgcagg gaatagatcc tccggcctga ccctgcagcc taatccagag    9660
```

-continued

```
ttcagggtca gctcacacca cgtcgaccct ggtcagcatc cctagggcag ttccagacaa    9720
ggccggaggt ctcctcttgc cctccagggg gtgacattgc acacagacat cactcaggaa    9780
acggattccc ctggacagga acctggcttt gctaaggaag tggaggtgga gcctggtttc    9840
catcccttgc tccaacagac ccttctgatc tctcccacat acctgctctg ttcctttctg    9900
ggtcctatga ggaccctgtt ctgccagggg tccctgtgca actccagact ccctcctggt    9960
accaccatgg ggaaggtggg gtgatcacag gacagtcagc ctcgcagaga cagagaccac   10020
ccaggactgt cagggagaac atggacaggc cctgagccgc agctcagcca acagacacgg   10080
agagggaggg tcccccctgga gccttcccca aggacagcag agcccagagt cacccacctc   10140
cctccaccac agtcctctct ttccaggaca cacaagacac ctcccccctcc acatgcagga   10200 tctgggact cctgagacct ctgggcctgg gtctccatcc ctgggtcagt ggcggggttg    10260
gtggtactgg agacagaggg ctggtccctc cccagccacc acccagtgag cctttttcta    10320
gcccccagag ccacctctgt caccttcctg ttgggcatca tcccaccttc ccagagccct   10380
ggagagcatg gggagacccg ggaccctgct gggtttctct gtcacaaagg aaataatcc    10440 ccctggtgtg acagacccaa ggacagaaca cagcagaggt cagcactggg gaagacaggt   10500
tgtcctccca ggggatgggg gtccatccac cttgccgaaa agatttgtct gaggaactga   10560
aaatagaagg gaaaaagag gagggacaaa agaggcagaa atgagagggg aggggacaga   10620
ggacacctga ataagacca cacccatgac ccacgtgatg ctgagaagta ctcctgccct    10680
aggaagagac tcagggcaga gggaggaagg acagcagacc agacagtcac agcagccttg   10740
acaaaacgtt cctggaactc aagctcttct ccacagagga ggacagagca gacagcgagg   10800
accatggagt ctccctcggc ccctcccccac agatggtgca tccctggca gaggctcctg   10860 ctcacaggtg aagggaggac aacctgggag agggtgggag gagggagctg gggtctcctg   10920
ggtaggacag ggctgtgaga cggacagagg gctcctgttg gagcctgaat agggaagagg   10980
acatcagaga gggacaggag tcacaccaga aaaatcaaat tgaactggaa ttggaaaggg   11040
gcaggaaaac ctcaagagtt ctattttcct agttaattgt cactggccac tacgttttta   11100
aaaatcataa taactgcatc agatgacact ttaaataaaa acataaccag ggcatgaaac   11160
actgtcctca tccgcctacc gcggacattg gaaaataagc cccaggctgt ggagggccct   11220
gggaaccctc atgaactcat ccacaggaat ctgcagcctg tcccaggcac tggggtgcaa   11280
ccaagatc                                                            11288
```

<210> SEQ ID NO 2
<211> LENGTH: 3774
<212> TYPE: DNA
<213> ORGANISM: Homo sapiens

<400> SEQUENCE: 2

```
aagcttttta gtgctttaga cagtgagctg gtctgtctaa cccaagtgac ctgggctcca     60
tactcagccc cagaagtgaa gggtgaagct ggtggagcc aaaccaggca agcctaccct    120
cagggctccc agtggcctga gaaccattgg acccaggacc cattacttct agggtaagga    180
aggtacaaac accagatcca accatggtct ggggggacag ctgtcaaatg cctaaaaata    240
tacctgggag aggagcaggc aaactatcac tgccccaggt tctctgaaca gaaacagagg    300
ggcaacccaa agtccaaatc caggtgagca ggtgcaccaa atgcccagag atatgacgag    360
gcaagaagtg aaggaaccac ccctgcatca aatgttttgc atgggaagga aaggggggtt    420
```

-continued

```
gctcatgttc ccaatccagg agaatgcatt tgggatctgc cttcttctca ctccttggtt      480
agcaagacta agcaaccagg actctggatt tggggaaaga cgtttatttg tggaggccag      540
tgatgacaat cccacgaggg cctaggtgaa gagggcagga aggctcgaga cactggggac      600
tgagtgaaaa ccacacccat gatctgcacc acccatggat gctccttcat tgctcacctt      660
tctgttgata tcagatggcc ccattttctg taccttcaca gaaggacaca ggctagggtc      720
tgtgcatggc cttcatcccc ggggccatgt gaggacagca ggtgggaaag atcatgggtc      780
ctcctgggtc ctgcagggcc agaacattca tcacccatac tgacctccta gatgggaatg      840
gcttccctgg ggctgggcca acggggcctg gcaggggag aaaggacgtc aggggacagg      900
gaggaagggt catcgagacc cagcctgaa ggttcttgtc tctgaccatc caggatttac       960
ttccctgcat ctacctttgg tcattttccc tcagcaatga ccagctctgc ttcctgatct     1020
cagcctccca ccctggacac agcacccag tccctggccc ggctgcatcc acccaatacc     1080
ctgataaccc aggacccatt acttctaggg taaggagggt ccaggagaca aagctgagg     1140 aaaggtctga agaagtcaca tctgtcctgg ccagagggga aaaccatca gatgctgaac     1200 caggagaatg ttgacccagg aaagggaccg aggacccaag aaaggagtca gaccaccagg     1260
gtttgcctga gaggaaggat caaggccccg agggaaagca gggctggctg catgtgcagg     1320
acactggtgg ggcatatgtg tcttagattc tccctgaatt cagtgtccct gccatggcca     1380
gactctctac tcaggcctgg acatgctgaa ataggacaat ggccttgtcc tctctcccca     1440
ccatttggca agagacataa aggacattcc aggacatgcc ttcctgggag gtccaggttc     1500
tctgtctcac acctcaggga ctgtagttac tgcatcagcc atggtaggtg ctgatctcac     1560
ccagcctgtc caggcccttc cactctccac tttgtgacca tgtccaggac cacccctcag     1620
atcctgagcc tgcaaatacc cccttgctgg gtgggtggat tcagtaaaca gtgagctcct     1680
atccagcccc cagagccacc tctgtcacct tcctgctggg catcatccca ccttcacaag     1740
cactaaagag catggggaga cctggctagc tgggtttctg catcacaaag aaaataatcc     1800
cccaggttcg gattcccagg gctctgtatg tggagctgac agacctgagg ccaggagata     1860
gcagaggtca gccctaggga gggtgggtca tccacccagg ggacagggt gcaccagcct      1920 tgctactgaa agggcctccc caggacacg ccatcagccc tgcctgagag ctttgctaaa     1980
cagcagtcag aggaggccat ggcagtggct gagctcctgc tccaggcccc aacagaccag     2040
accaacagca caatgcagtc cttccccaac gtcacaggtc accaaaggga aactgaggtg     2100
ctacctaacc ttagagccat caggggagat aacagcccaa tttcccaaac aggccagttt     2160
caatcccatg acaatgacct ctctgctctc attcttccca aaataggacg ctgattctcc     2220
cccaccatgg atttctccct tgtcccggga ccttttctg ccccctatga tctgggcact      2280
cctgacacac acctcctctc tggtgacata tcagggtccc tcactgtcaa gcagtccaga     2340
aaggacagaa ccttggacag cgcccatctc agcttcaccc ttcctccttc acagggttca     2400
gggcaaagaa taaatggcag aggccagtga gcccagagat ggtgacaggc agtgacccag     2460
gggcagatgc ctggagcagg agctggcggg gccacaggga gaaggtgatg caggaaggga     2520
aacccagaaa tgggcaggaa aggaggacac aggctctgtg gggctgcagc ccaggggttgg    2580 actatgagtg tgaagccatc tcagcaagta aggccaggtc ccatgaacaa gagtgggagc     2640
acgtggcttc ctgctctgta tatggggtgg gggattccat gccccataga accagatggc     2700
cggggttcag atggagaagg agcaggacag gggatcccca ggataggagg accccagtgt     2760
ccccacccag gcaggtgact gatgaatggg catgcagggt cctcctgggc tgggctctcc     2820
```

```
ctttgtccct caggattcct tgaaggaaca tccggaagcc gaccacatct acctggtggg    2880
ttctggggag tccatgtaaa gccaggagct tgtgttgcta ggaggggtca tggcatgtgc    2940
tgggggcacc aaagagagaa acctgagggc aggcaggacc tggtctgagg aggcatggga    3000
gcccagatgg ggagatggat gtcaggaaag gctgccccat cagggagggt gatagcaatg    3060
gggggtctgt gggagtgggc acgtgggatt ccctgggctc tgccaagttc cctcccatag    3120
tcacaacctg gggacactgc ccatgaaggg gcgcctttgc ccagccagat gctgctggtt    3180
ctgcccatcc actaccctct ctgctccagc cactctgggg cttttctccag atgccctgga   3240 cagccctggc ctgggcctgt cccctgagag gtgttgggag aagctgagtc tctggggaca    3300
ctctcatcag agtctgaaag gcacatcagg aaacatccct ggtctccagg actaggcaat    3360
gaggaaaggg ccccagctcc tccctttgcc actgagaggg tcgaccctgg gtggccacag    3420
tgacttctgc gtctgtccca tgcaccctga aaccacaaca aaaccccagc ccagaccct    3480 gcaggtacaa tacatgtggg gacagtctgt acccagggga agccagttct ctcttcctag    3540
gagaccgggc tcagggctg tgcccggggc aggcgggggc agcacgtgcc tgtccttgag     3600
aactcgggac cttaagggtc tctgctctgt gaggcacagc aaggatcctt ctgtccagag    3660
atgaaagcag ctcctgcccc tcctctgacc tcttcctcct tcccaaatct caaccaacaa    3720
ataggtgttt caaatctcat catcaaatct tcatccatcc acatgagaaa gctt          3774

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence:
      oligonucleotide hybridizing to 5' region of CEA

<400> SEQUENCE: 3
ccctgtgatc tccaggacag ctcagtctcc gtccaatctc                                40

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:
      oligonucleotide hybridizing to 5' region of CEA

<400> SEQUENCE: 4
gtttcctgag tgatgtctgt gtgcaatg                                             28

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
cctggaactc aagcttgaat tctccacaga ggagg                                     35

<210> SEQ ID NO 6
<211> LENGTH: 7
<212> TYPE: DNA
<213> ORGANISM: Artificial Sequence
<220> FEATURE:
<223> OTHER INFORMATION: Description of Artificial Sequence: consensus
``` sequence A1 from DNA Sequence 1:3-11 (1990).

<400> SEQUENCE: 6 tatawaw                                                                    7

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:    consensus
      sequence A2ca1t  from DNA Sequence 1:3-11 (1990).

<400> SEQUENCE: 7
ttggcnnnnn ngcca                                                          15

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence:    consensus
      sequence A4a1t  from DNA Sequence 1:3-11 (1990).

<400> SEQUENCE: 8
rrrncchcac cctg                                                           14

<210> SEQ ID NO 9
<211> LENGTH: 8
<212> TYPE: DNA
<213> ORGANISM: Artificial Sequence
<220> FEATURE:
<223> OTHER INFORMATION: Description of Artificial Sequence:  consensus
      sequence B2  from DNA Sequence 1:3-11 (1990).

<400> SEQUENCE: 9 gtggwwwg                                                                   8

<210> SEQ ID NO 10
<211> LENGTH: 8
<212> TYPE: DNA
<213> ORGANISM: Artificial Sequence
<220> FEATURE:
<223> OTHER INFORMATION: Description of Artificial Sequence:  consensus
      sequence B4  from DNA Sequence 1:3-11 (1990).

<400> SEQUENCE: 10 gsswgscc                                                                   8

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:  consensus
      sequence B12 from DNA Sequence 1:3-11 (1990).

<400> SEQUENCE: 11 ccwwwwwwgg                                                                10

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence:    consensus
      sequence B15 from DNA Sequence 1:3-11 (1990).

```
<400> SEQUENCE: 12 gaaagy                                                                    6

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence:  consensus
      sequence B17 from DNA Sequence 1:3-11 (1990).

<400> SEQUENCE: 13 tcmytt                                                                    6

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence:  consensus
      sequence B18 from DNA Sequence 1:3-11 (1990).

<400> SEQUENCE: 14 ancctctcy                                                                 9

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence:  consensus
      sequence C5  from DNA Sequence 1:3-11 (1990).

<400> SEQUENCE: 15 gtgsggtg                                                                  8

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence: consensus
      sequence D9  from DNA Sequence 1:3-11 (1990).

<400> SEQUENCE: 16 rtgacgtr                                                                  8

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence:  consensus
      sequence E5 from DNA Sequence 1:3-11 (1990).

<400> SEQUENCE: 17
accnnnnnng gt                                                            12

<210> SEQ ID NO 18
<211> LENGTH: 6
<212> TYPE: DNA
<213> ORGANISM: Artificial Sequence
<220> FEATURE:
<223> OTHER INFORMATION: Description of Artificial Sequence:  consensus
      sequence F2  from DNA Sequence 1:3-11 (1990).
```

```
<400> SEQUENCE: 18 tgrmcc                                                                    6

<210> SEQ ID NO 19
<211> LENGTH: 8
<212> TYPE: DNA
<213> ORGANISM: Artificial Sequence
<220> FEATURE:
<223> OTHER INFORMATION: Description of Artificial Sequence:  consensus
      sequence F6 from DNA Sequence 1:3-11 (1990).

<400> SEQUENCE: 19 tcntactc                                                                  8

<210> SEQ ID NO 20
<211> LENGTH: 8
<212> TYPE: DNA
<213> ORGANISM: Artificial Sequence
<220> FEATURE:
<223> OTHER INFORMATION: Description of Artificial Sequence:  consensus
      sequence F7  from DNA Sequence 1:3-11 (1990).

<400> SEQUENCE: 20 tgtttgct                                                                  8

<210> SEQ ID NO 21
<211> LENGTH: 5
<212> TYPE: DNA
<213> ORGANISM: Artificial Sequence
<220> FEATURE:
<223> OTHER INFORMATION: Description of Artificial Sequence:  consensus
      sequence F9  from DNA Sequence 1:3-11 (1990).

<400> SEQUENCE: 21 tcact                                                                     5

<210> SEQ ID NO 22
<211> LENGTH: 9
<212> TYPE: DNA
<213> ORGANISM: Artificial Sequence
<220> FEATURE:
<223> OTHER INFORMATION: Description of Artificial Sequence:  consensus
      sequence F10  from DNA Sequence 1:3-11 (1990).

<400> SEQUENCE: 22 wtstgggaw                                                                 9

<210> SEQ ID NO 23
<211> LENGTH: 8
<212> TYPE: DNA
<213> ORGANISM: Artificial Sequence
<220> FEATURE:
<223> OTHER INFORMATION: Description of Artificial Sequence: consensus
      sequence G2 from DNA Sequence 1:3-11 (1990).

<400> SEQUENCE: 23 aanccaaa                                                                  8

<210> SEQ ID NO 24
<211> LENGTH: 6
<212> TYPE: DNA
<213> ORGANISM: Artificial Sequence
<220> FEATURE:
<223> OTHER INFORMATION: Description of Artificial Sequence:  consensus
      sequence G7  from DNA Sequence 1:3-11 (1990).

<400> SEQUENCE: 24
```

```
gataag                                                              6

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: consensus
      sequence H1 from DNA Sequence 1:3-11 (1990).

<400> SEQUENCE: 25
rnynncnngy ngktnyn                                                 17
```